US012216962B2

(12) United States Patent
Li et al.

(10) Patent No.: US 12,216,962 B2
(45) Date of Patent: Feb. 4, 2025

(54) AUTOMATIC QUANTITATIVE FOOD INTAKE TRACKING

(71) Applicant: Meta Platforms Technologies, LLC, Menlo Park, CA (US)

(72) Inventors: Wen Li, Foster City, CA (US); John Rumsfeld, San Francisco, CA (US); Charles Liam Goudge, Menlo Park, CA (US); Freddy Abnousi, Menlo Park, CA (US)

(73) Assignee: Meta Platforms Technologies, LLC, Menlo Park, CA (US)

( * ) Notice: Subject to any disclaimer, the term of this patent is extended or adjusted under 35 U.S.C. 154(b) by 286 days.

(21) Appl. No.: 17/867,863

(22) Filed: Jul. 19, 2022

(65) Prior Publication Data

US 2024/0028294 A1   Jan. 25, 2024

(51) Int. Cl.
  G06F 3/16    (2006.01)
  G10L 15/22   (2006.01)
  G10L 15/30   (2013.01)

(52) U.S. Cl.
  CPC .............. G06F 3/167 (2013.01); G10L 15/22 (2013.01); G10L 15/30 (2013.01); *G10L 2015/223* (2013.01)

(58) Field of Classification Search
  None
  See application file for complete search history.

(56) References Cited

U.S. PATENT DOCUMENTS

| 9,189,021 | B2 | 11/2015 | Jerauld |
| 9,314,206 | B2 | 4/2016 | Menczel et al. |
| 9,529,385 | B2 | 12/2016 | Connor |
| 9,646,511 | B2 | 5/2017 | Jerauld |
| 9,916,520 | B2 | 3/2018 | Divakaran et al. |
| 10,803,315 | B2 | 10/2020 | Cho et al. |

(Continued)

OTHER PUBLICATIONS

Adam S., et al., "Investigating Novel Proximity Monitoring Techniques Using Ubiquitous Sensor Technology," Systems and Information Engineeringdesign Symposium (SIEDS), Apr. 29, 2021, 6 pages.

(Continued)

*Primary Examiner* — Stella L. Woo
(74) *Attorney, Agent, or Firm* — Potomac Law Group, PLLC; Dannon G. Allbee

(57) ABSTRACT

Aspects of the present disclosure are directed to quantitatively tracking food intake using smart glasses and/or other wearable devices. In some implementations, the smart glasses can include an image capture device, such as a camera, that can seamlessly capture images of food being eaten by the user. A computing device in communication with the smart glasses (or the smart glasses themselves) can identify the type and volume of food being eaten by applying object recognition and volume estimation techniques to the images. Additionally or alternatively, the smart glasses and/or other wearable devices can track a user's eating patterns through the number of bites taken throughout the day by capturing and analyzing hand-to-mouth motions and chewing. The computing device can log the type of food, volume of food, and/or number of bites taken and compute statistics that can be displayed to the user on the smart glasses.

17 Claims, 15 Drawing Sheets

(56) References Cited

U.S. PATENT DOCUMENTS

| | | | |
|---|---|---|---|
| 11,064,942 B1* | 7/2021 | Catani | A61B 5/14532 |
| 2011/0276312 A1 | 11/2011 | Shalon et al. | |
| 2014/0147829 A1* | 5/2014 | Jerauld | G06F 3/011 |
| | | | 434/430 |
| 2016/0012749 A1* | 1/2016 | Connor | A61B 5/24 |
| | | | 600/27 |
| 2016/0148535 A1 | 5/2016 | Ashby | |
| 2016/0330223 A1* | 11/2016 | Sridhara | G06F 21/566 |
| 2017/0270820 A1* | 9/2017 | Ashby | A61B 5/7465 |
| 2018/0242908 A1* | 8/2018 | Sazonov | A61B 5/4542 |
| 2019/0192073 A1* | 6/2019 | Shi | G06F 1/163 |
| 2021/0249116 A1 | 8/2021 | Connor | |
| 2022/0143314 A1* | 5/2022 | Lintereur | A61B 5/4839 |
| 2023/0058760 A1* | 2/2023 | Ishigaki | G16H 20/60 |
| 2023/0223130 A1* | 7/2023 | Utsumi | G16H 20/60 |
| | | | 705/2 |
| 2024/0177824 A1 | 5/2024 | Kim et al. | |

OTHER PUBLICATIONS

International Preliminary Report on Patentability for International Application No. PCT/US2022/043917, mailed Apr. 4, 2024, 9 pages.

International Search report and Written Opinion for International Application No. PCT/US2022/043917, mailed Dec. 12, 2022, 11 pages.

* cited by examiner

AUTOMATIC QUANTITATIVE FOOD INTAKE TRACKING

TECHNICAL FIELD

The present disclosure is directed to automatically and quantitatively tracking food intake, e.g., using smart glasses and/or other wearable devices.

BACKGROUND

Food intake tracking has become increasingly popular as people have become more health-focused and conscious of the effects of food on their bodies. Because manually tracking food intake throughout a day, week, or even month can become an onerous task, a number of approaches have been proposed to simplify the process. For example, software developers have created applications usable on a mobile device that allow users to self-report their food intake. For example, a user can use an application to search a database for the type of food that was eaten at each meal and enter the serving size consumed. The application can then populate generalized nutritional data associated with the type and volume of the food eaten, and aggregate it to allow for tracking of calories, fat, carbohydrates, etc., that were consumed over the course of a day.

BRIEF DESCRIPTION OF THE DRAWINGS

The techniques introduced here may be better understood by referring to the following Detailed Description in conjunction with the accompanying drawings, in which like reference numerals indicate identical or functionally similar elements.

DETAILED DESCRIPTION

Figure 1:
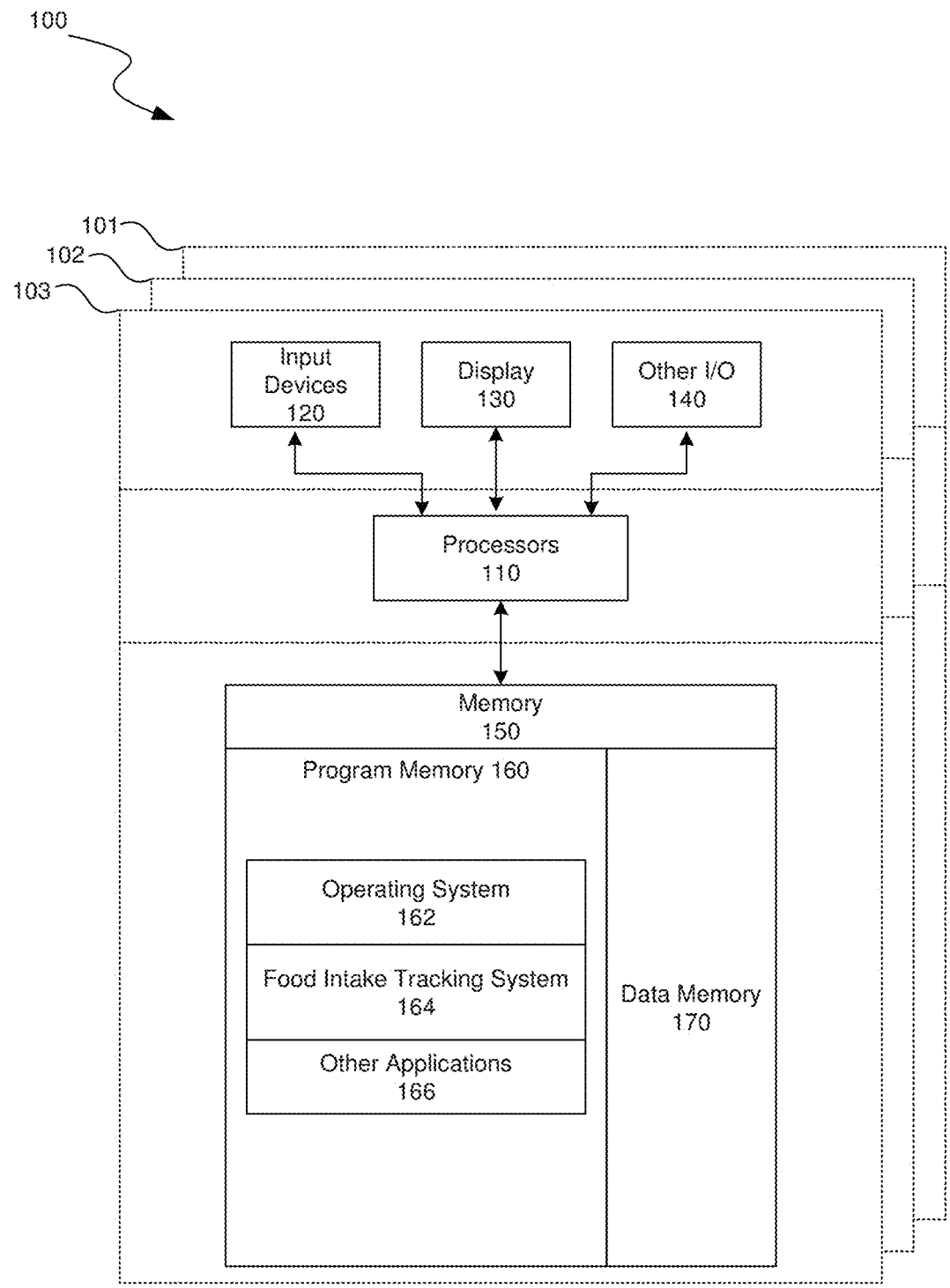
FIG. 1 is a block diagram illustrating an overview of devices on which some implementations of the present technology can operate.

Aspects of the present disclosure are directed to quantitatively tracking food intake using smart glasses. In some implementations, the smart glasses can include an image capture device, such as a camera, that can seamlessly capture images of food being eaten by the user. A computing device in communication with the smart glasses (or the smart glasses themselves) can identify the type of food being eaten by applying object recognition to the images. The computing device can further perform volume estimation on the food using the images. The computing device can log the type of food and volume of food and compute statistics, such as total calories consumed throughout the day, that can be displayed to the user on the smart glasses.

Additionally or alternatively, the smart glasses and/or other wearable devices can track a user's eating patterns through the number of bites taken throughout the day by capturing and analyzing hand-to-mouth motions and chewing. The computing device (or the smart glasses themselves) can use these eating patterns to calculate statistics, such as whether a user has eaten more or less than usual at a particular time of the day. The smart glasses can display such statistics seamlessly to the user while being worn.

Although applications exist that allow a user to manually enter their food intake throughout the day on a mobile device, such applications have a number of drawbacks. For example, such applications rely on self-reporting of food intake, which often results in considerable underreporting of snacks and volumes of food consumed. In addition, these applications require the user to manually enter the type and volume of each food item eaten, which can be inconvenient and time consuming. Thus, existing applications for food intake tracking can be significantly inaccurate.

Smart glasses or other wearable devices provide a number of benefits for food intake tracking that cannot be realized by existing applications. For example, smart glasses can easily and conveniently be worn and removed throughout the day with minimal disruption or intrusion into a user's normal daily habits. Food intake tracking by wearable devices requires minimal user input, and any user input needed can be given audibly by the user, eliminating the need for other input devices, such as a keyboard. For example, users can provide audible input regarding whether food items predicted using wearable devices are correct, allowing for further training of a machine learning model used to perform automatic object recognition on future food items. In addition, users can provide feedback regarding whether the volume of the food predicted by applying depth estimation techniques to images of the food to further refine such techniques. Further, tracking food intake using wearable devices can be more accurate in terms of logging all food eaten by the user throughout the day, as well as in estimating the volume of food being consumed. Such accuracy can be highly useful for users trying to lose weight, diabetics tracking their sugar intake, users with high blood pressure tracking their sodium intake, and the like.

Embodiments of the disclosed technology may include or be implemented in conjunction with an artificial reality system. Artificial reality or extra reality (XR) is a form of reality that has been adjusted in some manner before presentation to a user, which may include, e.g., virtual reality (VR), augmented reality (AR), mixed reality (MR), hybrid reality, or some combination and/or derivatives thereof. Artificial reality content may include completely generated content or generated content combined with captured content (e.g., real-world photographs). The artificial reality content may include video, audio, haptic feedback, or some combination thereof, any of which may be presented in a single channel or in multiple channels (such as stereo video that produces a three-dimensional effect to the viewer). Additionally, in some embodiments, artificial reality may be associated with applications, products, accessories, services, or some combination thereof, that are, e.g., used to create content in an artificial reality and/or used in (e.g., perform activities in) an artificial reality. The artificial reality system that provides the artificial reality content may be implemented on various platforms, including a head-mounted display (HMD) connected to a host computer system, a standalone HMD, a mobile device or computing system, a "cave" environment or other projection system, or any other hardware platform capable of providing artificial reality content to one or more viewers.

"Virtual reality" or "VR," as used herein, refers to an immersive experience where a user's visual input is controlled by a computing system. "Augmented reality" or "AR" refers to systems where a user views images of the real world after they have passed through a computing system. For example, a tablet with a camera on the back can capture images of the real world and then display the images on the screen on the opposite side of the tablet from the camera. The tablet can process and adjust or "augment" the images as they pass through the system, such as by adding virtual objects. "Mixed reality" or "MR" refers to systems where light entering a user's eye is partially generated by a computing system and partially composes light reflected off objects in the real world. For example, a MR headset could be shaped as a pair of glasses with a pass-through display, which allows light from the real world to pass through a waveguide that simultaneously emits light from a projector in the MR headset, allowing the MR headset to present virtual objects intermixed with the real objects the user can see. "Artificial reality," "extra reality," or "XR," as used herein, refers to any of VR, AR, MR, or any combination or hybrid thereof.

Several implementations are discussed below in more detail in reference to the figures. FIG. 1 is a block diagram illustrating an overview of devices on which some implementations of the disclosed technology can operate. The devices can comprise hardware components of a computing system 100 that quantitatively tracks food intake using smart glasses. In various implementations, computing system 100 can include a single computing device 103 or multiple computing devices (e.g., computing device 101, computing device 102, and computing device 103) that communicate over wired or wireless channels to distribute processing and share input data. In some implementations, computing system 100 can include a stand-alone headset capable of providing a computer created or augmented experience for a user without the need for external processing or sensors. In other implementations, computing system 100 can include multiple computing devices such as a headset and a core processing component (such as a console, mobile device, or server system) where some processing operations are performed on the headset and others are offloaded to the core processing component. Example headsets are described below in relation to FIGS. 2A and 2B. In some implementations, position and environment data can be gathered only by sensors incorporated in the headset device, while in other implementations one or more of the non-headset computing devices can include sensor components that can track environment or position data.

Computing system 100 can include one or more processor(s) 110 (e.g., central processing units (CPUs), graphical processing units (GPUs), holographic processing units (HPUs), etc.) Processors 110 can be a single processing unit or multiple processing units in a device or distributed across multiple devices (e.g., distributed across two or more of computing devices 101-103).

Computing system 100 can include one or more input devices 120 that provide input to the processors 110, notifying them of actions. The actions can be mediated by a hardware controller that interprets the signals received from the input device and communicates the information to the processors 110 using a communication protocol. Each input device 120 can include, for example, a mouse, a keyboard, a touchscreen, a touchpad, a wearable input device (e.g., a haptics glove, a bracelet, a ring, an earring, a necklace, a watch, etc.), a camera (or other light-based input device, e.g., an infrared sensor), a microphone, or other user input devices.

Processors 110 can be coupled to other hardware devices, for example, with the use of an internal or external bus, such as a PCI bus, SCSI bus, or wireless connection. The processors 110 can communicate with a hardware controller for devices, such as for a display 130. Display 130 can be used to display text and graphics. In some implementations, display 130 includes the input device as part of the display, such as when the input device is a touchscreen or is equipped with an eye direction monitoring system. In some implementations, the display is separate from the input device. Examples of display devices are: an LCD display screen, an LED display screen, a projected, holographic, or augmented reality display (such as a heads-up display device or a head-mounted device), and so on. Other I/O devices 140 can also be coupled to the processor, such as a network chip or card, video chip or card, audio chip or card, USB, firewire or other external device, camera, printer, speakers, CD-ROM drive, DVD drive, disk drive, etc.

In some implementations, input from the I/O devices 140, such as cameras, depth sensors, IMU sensor, GPS units, LiDAR or other time-of-flights sensors, etc. can be used by the computing system 100 to identify and map the physical environment of the user while tracking the user's location within that environment. This simultaneous localization and mapping (SLAM) system can generate maps (e.g., topologies, girds, etc.) for an area (which may be a room, building, outdoor space, etc.) and/or obtain maps previously generated by computing system 100 or another computing system that had mapped the area. The SLAM system can track the user within the area based on factors such as GPS data, matching identified objects and structures to mapped objects and structures, monitoring acceleration and other position changes, etc.

Computing system 100 can include a communication device capable of communicating wirelessly or wire-based with other local computing devices or a network node. The communication device can communicate with another device or a server through a network using, for example, TCP/IP protocols. Computing system 100 can utilize the communication device to distribute operations across multiple network devices.

The processors 110 can have access to a memory 150, which can be contained on one of the computing devices of computing system 100 or can be distributed across of the multiple computing devices of computing system 100 or other external devices. A memory includes one or more hardware devices for volatile or non-volatile storage, and can include both read-only and writable memory. For example, a memory can include one or more of random access memory (RAM), various caches, CPU registers, read-only memory (ROM), and writable non-volatile memory, such as flash memory, hard drives, floppy disks, CDs, DVDs, magnetic storage devices, tape drives, and so forth. A memory is not a propagating signal divorced from underlying hardware; a memory is thus non-transitory. Memory 150 can include program memory 160 that stores programs and software, such as an operating system 162, a food intake tracking system 164, and other application programs 166. Memory 150 can also include data memory 170 that can include, e.g., food image data, motion data, chewing data, baseline data, feature data, nutritional data, configuration data, settings, user options or preferences, etc., which can be provided to the program memory 160 or any element of the computing system 100.

Some implementations can be operational with numerous other computing system environments or configurations. Examples of computing systems, environments, and/or configurations that may be suitable for use with the technology include, but are not limited to, XR headsets, personal computers, server computers, handheld or laptop devices, cellular telephones, wearable electronics, gaming consoles, tablet devices, multiprocessor systems, microprocessor-based systems, set-top boxes, programmable consumer electronics, network PCs, minicomputers, mainframe computers, distributed computing environments that include any of the above systems or devices, or the like.

Figure 2A:
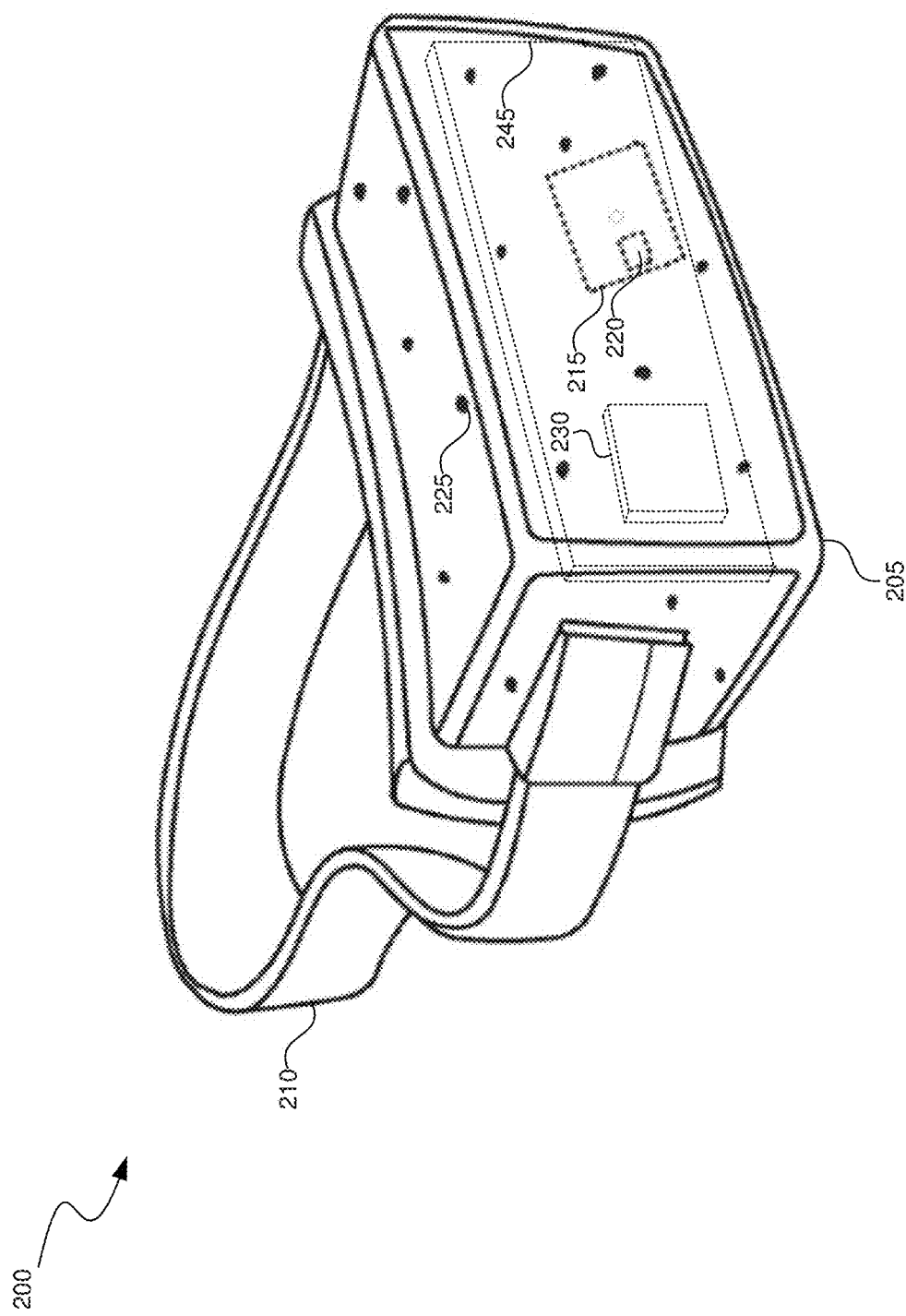
FIG. 2A is a wire diagram illustrating a virtual reality headset which can be used in some implementations of the present technology.

FIG. 2A is a wire diagram of a virtual reality head-mounted display (HMD) 200, in accordance with some embodiments. The HMD 200 includes a front rigid body 205 and a band 210. The front rigid body 205 includes one or more electronic display elements of an electronic display 245, an inertial motion unit (IMU) 215, one or more position sensors 220, locators 225, and one or more compute units 230. The position sensors 220, the IMU 215, and compute units 230 may be internal to the HMD 200 and may not be visible to the user. In various implementations, the IMU 215, position sensors 220, and locators 225 can track movement and location of the HMD 200 in the real world and in an artificial reality environment in three degrees of freedom (3DoF) or six degrees of freedom (6DoF). For example, the locators 225 can emit infrared light beams which create light points on real objects around the HMD 200. As another example, the IMU 215 can include e.g., one or more accelerometers, gyroscopes, magnetometers, other non-camera-based position, force, or orientation sensors, or combinations thereof. One or more cameras (not shown) integrated with the HMD 200 can detect the light points. Compute units 230 in the HMD 200 can use the detected light points to extrapolate position and movement of the HMD 200 as well as to identify the shape and position of the real objects surrounding the HMD 200.

The electronic display 245 can be integrated with the front rigid body 205 and can provide image light to a user as dictated by the compute units 230. In various embodiments, the electronic display 245 can be a single electronic display or multiple electronic displays (e.g., a display for each user eye). Examples of the electronic display 245 include: a liquid crystal display (LCD), an organic light-emitting diode (OLED) display, an active-matrix organic light-emitting diode display (AMOLED), a display including one or more quantum dot light-emitting diode (QOLED) sub-pixels, a projector unit (e.g., microLED, LASER, etc.), some other display, or some combination thereof.

In some implementations, the HMD 200 can be coupled to a core processing component such as a personal computer (PC) (not shown) and/or one or more external sensors (not shown). The external sensors can monitor the HMD 200 (e.g., via light emitted from the HMD 200) which the PC can use, in combination with output from the IMU 215 and position sensors 220, to determine the location and movement of the HMD 200.

Figure 2B:
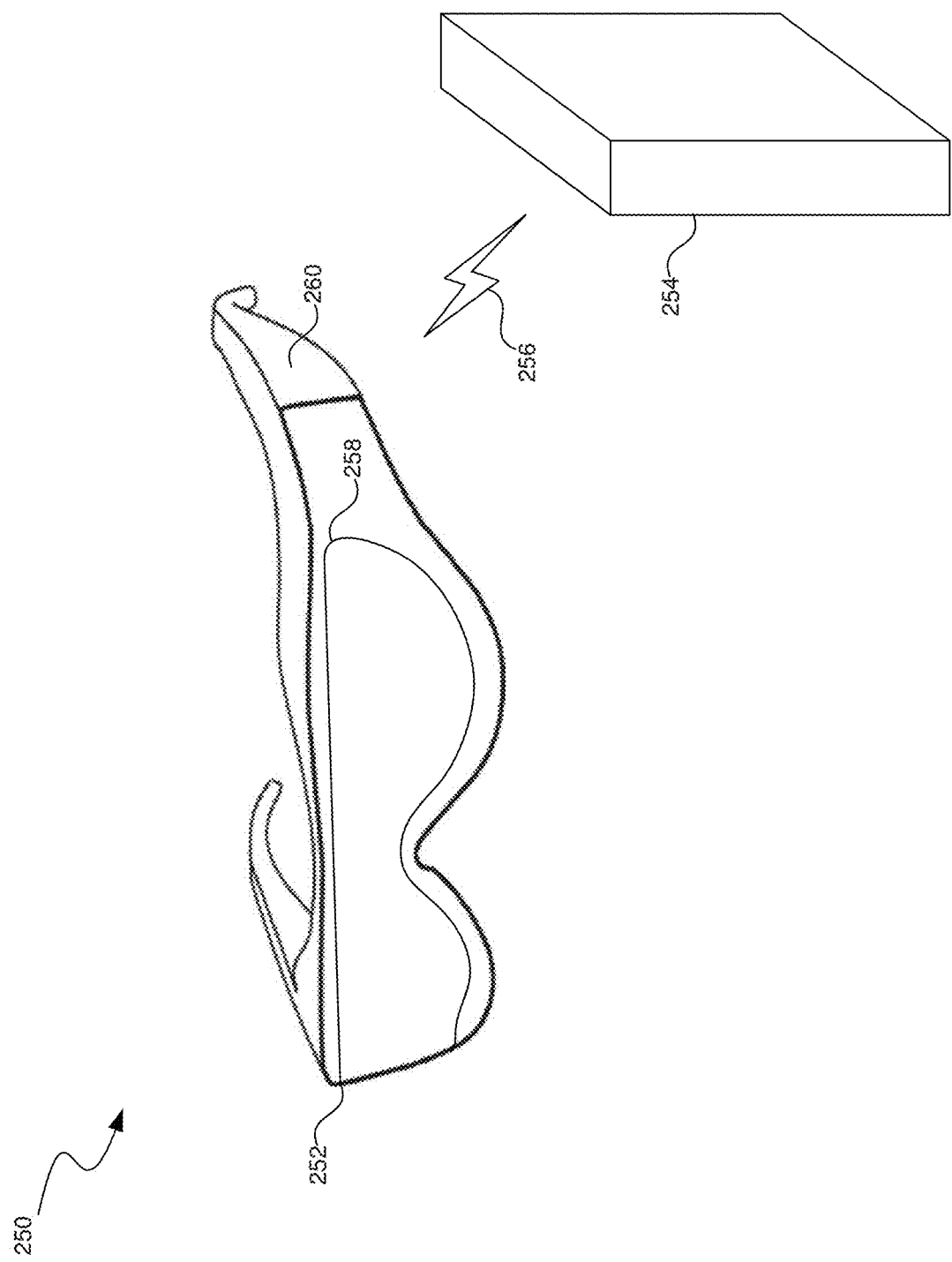
FIG. 2B is a wire diagram illustrating a mixed reality headset which can be used in some implementations of the present technology.

FIG. 2B is a wire diagram of a mixed reality HMD system 250 which includes a mixed reality HMD 252 and a core processing component 254. The mixed reality HMD 252 and the core processing component 254 can communicate via a wireless connection (e.g., a 60 GHz link) as indicated by link 256. In other implementations, the mixed reality system 250 includes a headset only, without an external compute device or includes other wired or wireless connections between the mixed reality HMD 252 and the core processing component 254. The mixed reality HMD 252 includes a pass-through display 258 and a frame 260. The frame 260 can house various electronic components (not shown) such as light projectors (e.g., LASERs, LEDs, etc.), cameras, eye-tracking sensors, MEMS components, networking components, etc. In some implementations, the HMD 200 or the mixed reality HMD 252 can be "smart glasses," as described further herein.

The projectors can be coupled to the pass-through display 258, e.g., via optical elements, to display media to a user. The optical elements can include one or more waveguide assemblies, reflectors, lenses, mirrors, collimators, gratings, etc., for directing light from the projectors to a user's eye. Image data can be transmitted from the core processing component 254 via link 256 to HMD 252. Controllers in the HMD 252 can convert the image data into light pulses from the projectors, which can be transmitted via the optical elements as output light to the user's eye. The output light can mix with light that passes through the display 258, allowing the output light to present virtual objects that appear as if they exist in the real world.

Similarly to the HMD 200, the HMD system 250 can also include motion and position tracking units, cameras, light sources, etc., which allow the HMD system 250 to, e.g., track itself in 3DoF or 6DoF, track portions of the user (e.g., hands, feet, head, or other body parts), map virtual objects to appear as stationary as the HMD 252 moves, and have virtual objects react to gestures and other real-world objects.

Figure 2C:
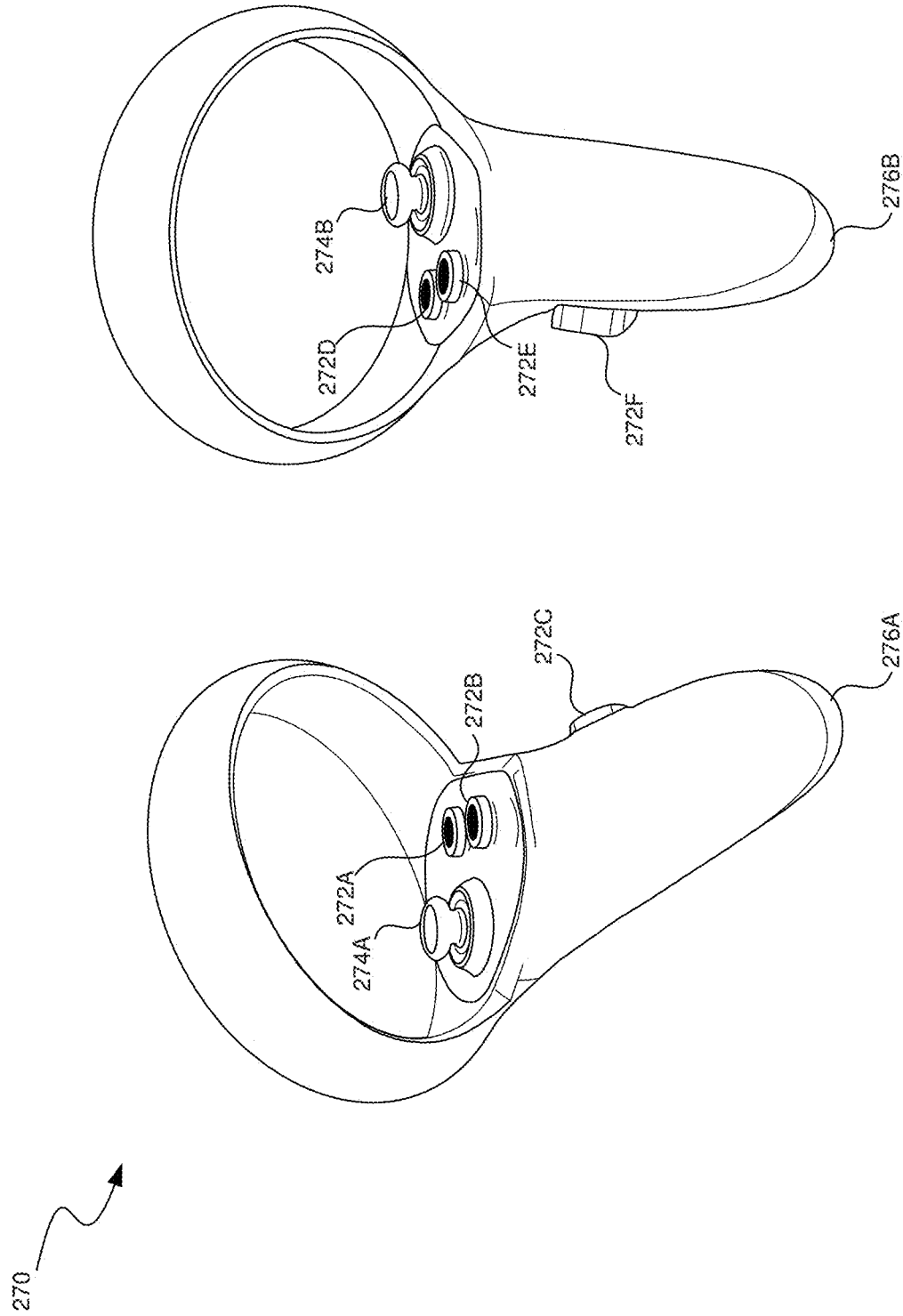
FIG. 2C is a wire diagram illustrating controllers which, in some implementations, a user can hold in one or both hands to interact with an artificial reality environment.

FIG. 2C illustrates controllers 270 (including controller 276A and 276B), which, in some implementations, a user can hold in one or both hands to interact with an artificial reality environment presented by the HMD 200 and/or HMD 250. The controllers 270 can be in communication with the HMDs, either directly or via an external device (e.g., core processing component 254). The controllers can have their own IMU units, position sensors, and/or can emit further light points. The HMD 200 or 250, external sensors, or sensors in the controllers can track these controller light points to determine the controller positions and/or orientations (e.g., to track the controllers in 3DoF or 6DoF). The compute units 230 in the HMD 200 or the core processing component 254 can use this tracking, in combination with IMU and position output, to monitor hand positions and motions of the user. The controllers can also include various buttons (e.g., buttons 272A-F) and/or joysticks (e.g., joysticks 274A-B), which a user can actuate to provide input and interact with objects.

In various implementations, the HMD 200 or 250 can also include additional subsystems, such as an eye tracking unit, an audio system, various network components, etc., to monitor indications of user interactions and intentions. For example, in some implementations, instead of or in addition to controllers, one or more cameras included in the HMD 200 or 250, or from external cameras, can monitor the positions and poses of the user's hands to determine gestures and other hand and body motions. As another example, one or more light sources can illuminate either or both of the user's eyes and the HMD 200 or 250 can use eye-facing cameras to capture a reflection of this light to determine eye position (e.g., based on set of reflections around the user's cornea), modeling the user's eye and determining a gaze direction.

In some implementations described herein, a user can wear a wearable device to track hand, wrist, and/or arm motions or orientations, such as a watch, a bracelet, a ring, an armband, etc. The wearable device can include one or more sensors of an inertial measurement unit (IMU), such as one or more accelerometers, gyroscopes, magnetometers, compasses, or other position, force, motion, or orientation sensors, or combinations thereof.

Figure 3:
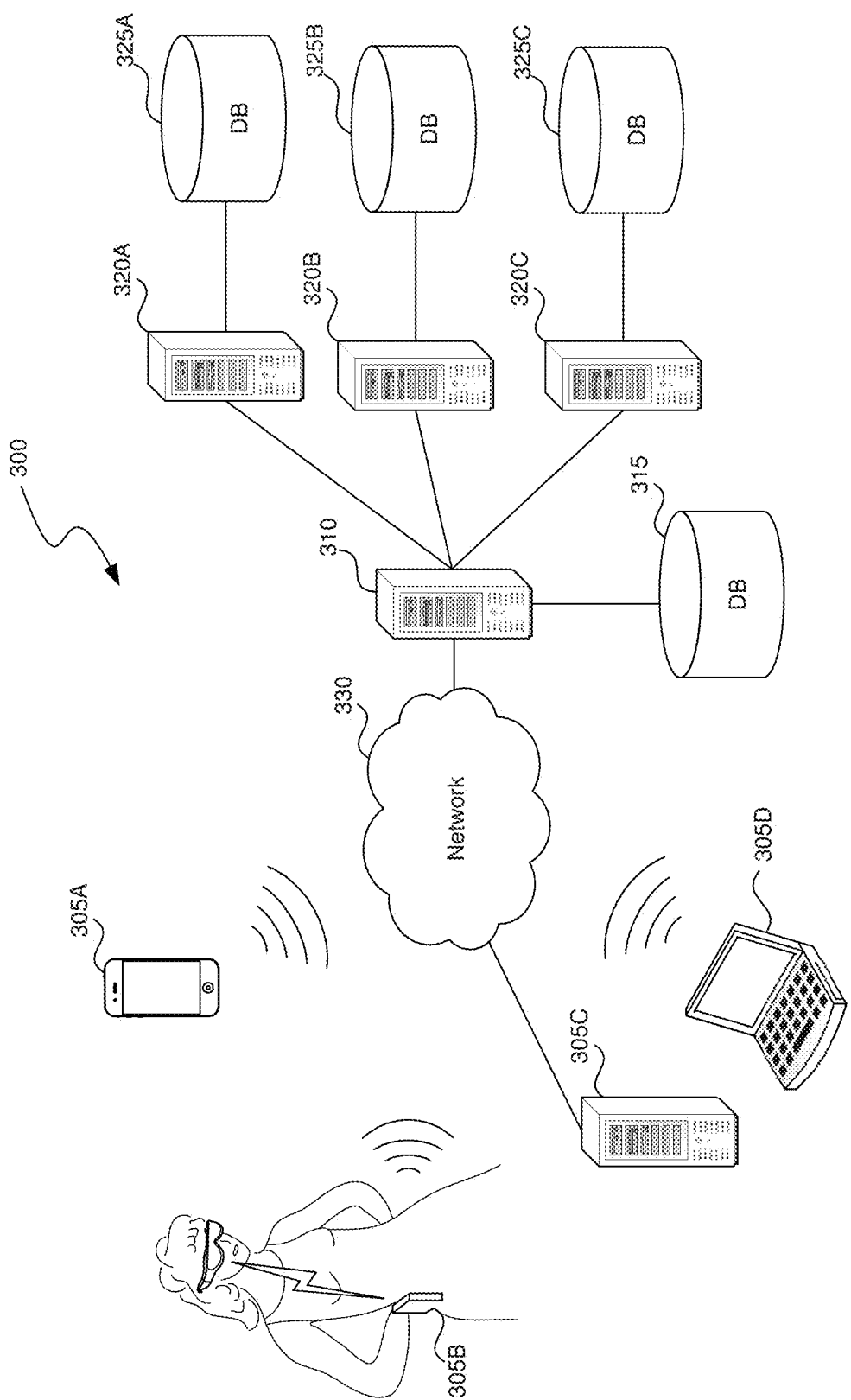
FIG. 3 is a block diagram illustrating an overview of an environment in which some implementations of the present technology can operate.

FIG. 3 is a block diagram illustrating an overview of an environment 300 in which some implementations of the disclosed technology can operate. Environment 300 can include one or more client computing devices 305A-D, examples of which can include computing system 100. In some implementations, some of the client computing devices (e.g., client computing device 305B) can be the HMD 200 or the HMD system 250. Client computing devices 305 can operate in a networked environment using logical connections through network 330 to one or more remote computers, such as a server computing device.

In some implementations, server 310 can be an edge server which receives client requests and coordinates fulfillment of those requests through other servers, such as servers 320A-C. Server computing devices 310 and 320 can comprise computing systems, such as computing system 100. Though each server computing device 310 and 320 is displayed logically as a single server, server computing devices can each be a distributed computing environment encompassing multiple computing devices located at the same or at geographically disparate physical locations.

Client computing devices 305 and server computing devices 310 and 320 can each act as a server or client to other server/client device(s). Server 310 can connect to a database 315. Servers 320A-C can each connect to a corresponding database 325A-C. As discussed above, each server 310 or 320 can correspond to a group of servers, and each of these servers can share a database or can have their own database. Though databases 315 and 325 are displayed logically as single units, databases 315 and 325 can each be a distributed computing environment encompassing multiple computing devices, can be located within their corresponding server, or can be located at the same or at geographically disparate physical locations.

Network 330 can be a local area network (LAN), a wide area network (WAN), a mesh network, a hybrid network, or other wired or wireless networks. Network 330 may be the Internet or some other public or private network. Client computing devices 305 can be connected to network 330 through a network interface, such as by wired or wireless communication. While the connections between server 310 and servers 320 are shown as separate connections, these connections can be any kind of local, wide area, wired, or wireless network, including network 330 or a separate public or private network.

Figure 4A:
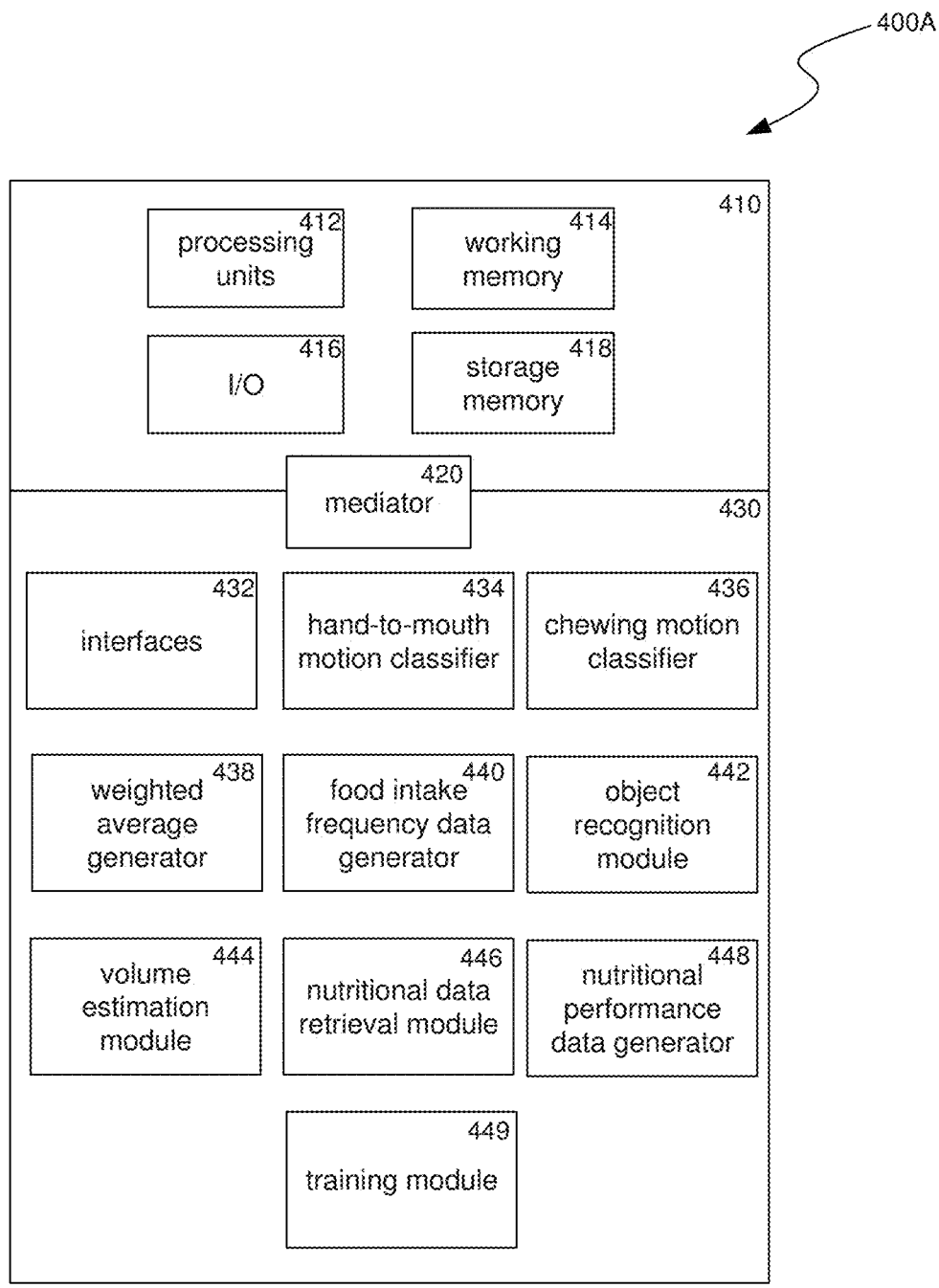
FIG. 4A is a block diagram illustrating components which, in some implementations, can be used in a system employing the disclosed technology.

FIG. 4A is a block diagram illustrating components 400 which, in some implementations, can be used in a system employing the disclosed technology. Components 400 can be included in one device of computing system 100 or can be distributed across multiple of the devices of computing system 100. The components 400 include hardware 410, mediator 420, and specialized components 430. As discussed above, a system implementing the disclosed technology can use various hardware including processing units 412, working memory 414, input and output devices 416 (e.g., cameras, displays, IMU units, network connections, etc.), and storage memory 418. In various implementations, storage memory 418 can be one or more of: local devices, interfaces to remote storage devices, or combinations thereof. For example, storage memory 418 can be one or more hard drives or flash drives accessible through a system bus or can be a cloud storage provider (such as in storage 315 or 325) or other network storage accessible via one or more communications networks. In various implementations, components 400 can be implemented in a client computing device such as client computing devices 305 or on a server computing device, such as server computing device 310 or 320.

Mediator 420 can include components which mediate resources between hardware 410 and specialized components 430. For example, mediator 420 can include an operating system, services, drivers, a basic input output system (BIOS), controller circuits, or other hardware or software systems.

Specialized components 430 can include software or hardware configured to perform operations for quantitatively tracking food intake using smart glasses. Specialized components 430 can include hand-to-mouth motion classifier 434, chewing motion classifier 436, weighted average generator 438, food intake frequency data generator 440, object recognition module 442, volume estimation module 444, nutritional data retrieval module 446, nutritional performance data generator 448, training module 449, and components and APIs which can be used for providing user interfaces, transferring data, and controlling the specialized components, such as interfaces 432. In some implementations, components 400 can be in a computing system that is distributed across multiple computing devices or can be an interface to a server-based application executing one or more of specialized components 430. Although depicted as separate components, specialized components 430 may be logical or other nonphysical differentiations of functions and/or may be submodules or code-blocks of one or more applications.

Hand-to-mouth motion classifier 434 can obtain motion data indicative of motion by the user. The motion data can be captured by any suitable device collocated with components 400, such as in I/O 416, (not shown) or separate from components 400. For example, the motion data can be captured by one or more image capture devices and/or one or more sensors of an inertial measurement unit (IMU) integral with either or both of smart glasses or a wearable device positioned on the wrist or hand, such as a smart watch. Further details regarding how the motion data can be captured are described herein with respect to block 502 of FIG. 5A.

Hand-to-mouth motion classifier 434 can analyze the motion data and determine whether the motion data is indicative of hand-to-mouth motions. For example, hand-to-mouth motion classifier 434 can perform object recognition on the captured image(s) to identify a user's hand, and determine that the identified hand is approaching the user's mouth below the smart glasses. In another example, when the motion data is captured by a gyroscope and accelerometer in an IMU, hand-to-mouth motion classifier 434 can analyze the motion data to identify features or patterns indicative of a hand-to-mouth motion, as trained by a machine learning model. Further details regarding how hand-to-mouth motion classifier 434 can identify hand-to-mouth motions are described herein with respect to block 504 of FIG. 5A. In some implementations, hand-to-mouth motion classifier 434 can facilitate display of the cumulative number of hand-to-mouth motions for a meal or a day to a user via interfaces 432, or other statistics.

Chewing motion classifier 436 can identify chewing motions by the user. The chewing motion data can be captured by any suitable device collocated with components 400, such as in I/O 416, or separate from components 400. For example, chewing motion classifier 436 can obtain an audio signal input from a microphone and analyze the audio signal using a machine learning model to identify sounds consistent with chewing. Alternatively or additionally, process 500A can analyze accelerometer data captured by an IMU to identify subtle repeated motions of a user's head consistent with up and down movement of the jaw. Further details regarding how chewing motion classifier 436 can identify chewing motions are described herein with respect to block 506 of FIG. 5A. In some implementations, chewing motion classifier 436 can facilitate display of the cumulative number of chewing motions for a meal or a day to a user via interfaces 432, or other statistics.

In some implementations, components 400 include a weighted average generator 438. Weighted average generator 438 can calculate a weighted average of the hand-to-mouth motions and the chewing motions. For example, process 500A can weigh the number of hand-to-mouth motions more heavily than the number of chewing motions. Such a weighted average can more accurately reflect the number of bites of food that are eaten, because the number of chewing motions made by a user can be affected by the texture or density of the food being eaten, and not necessarily by the amount of food. Further details regarding calculating a weighted average are described herein with respect to FIG. 5A.

Food intake frequency data generator 440 can generate food intake frequency data by comparing the hand-to-mouth motions and the chewing motions to baseline metrics. For example, food intake frequency data generator 440 can count the number of hand-to-mouth and/or chewing motions made and compare them to any baseline metric data available, including historical data associated with the user or other users. Further details regarding baseline metrics are described herein with respect to block 508 of FIG. 5A. In some implementations, food intake frequency data generator 440 can facilitate display of the food intake frequency data to a user via interfaces 432, for example. Further details regarding display of the food intake frequency data are described herein with respect to block 510 of FIG. 5A.

Object recognition module 442 can obtain at least one image of food. The at least one image of food can be obtained, for example, by one or more image capture devices (e.g., one or more cameras) capturing the field-of-view of the user. The image capture device(s), which can be included in I/O 416, can be collocated with or separate from components 400. Further details regarding capture of the one or more images of food are described herein with respect to block 512 of FIG. 5B.

Object recognition module 442 can identify a type of the food to be eaten by performing object recognition on the at least one image of food. Objection recognition module 442 can perform object recognition using any suitable method, such as by applying machine learning algorithms and/or deep learning models in order to learn the features of many different types of food, thus being able to predict and identify food within a particular image. Further details regarding object recognition techniques, as well as other data that can be used to identify a food type, are described herein with respect to block 514 of FIG. 5B. In some implementations, object recognition module 442 can facilitate display of the identified food type, as described further herein with respect to FIG. 5B.

Volume estimation module 444 can determine a volume of the food by performing volume estimation on the at least one image of food. Volume estimation module 444 can apply any known volume estimation method or combinations thereof to the one or more images of the food, including machine learning models. Further details regarding volume estimation techniques are described herein with respect to block 516 of FIG. 5B. In some implementations, volume estimation module 444 can facilitate display of the identified food type, as described further herein with respect to FIG. 5B.

Nutritional data retrieval module 446 can obtain nutritional data associated with the type of food and the volume of the food. The nutritional data can include metrics, for example, such as calories, total fat, saturated fat, sugar, carbohydrates, cholesterol, protein, sodium, vitamins, minerals, etc., adjusted for the identified volume of the food, as described further herein with respect to block 518 of FIG. 5B. In some implementations, nutritional data retrieval module 446 can adjust the nutritional data for the actual volume of food consumed, as determined by performing object recognition and volume estimation on any remaining food after the user is done eating, as described further herein with respect to FIG. 5B.

Nutritional performance data generator 448 can generate nutritional performance data by comparing the nutritional data to a nutritional benchmark for the user. The nutritional benchmark can be based on any desired goal by or for a user, as described further herein with respect to block 520 of FIG. 5B. In some implementations, nutritional performance data generator 448 can facilitate display of the nutritional performance data to a user via interfaces 432, for example, as described further herein with respect to block 522 of FIG. 5B.

Training module 449 can receive explicit or implicit feedback from the user regarding whether any of the data predicted by specialized components 430 is correct. For example, training module 449 can obtain feedback data regarding whether a hand-to-mouth motion has been properly identified, whether a chewing motion has been properly identified, whether the predicted food type is correct, or whether the predicted volume of the food is correct, or any combination thereof. Training module 449 can use this feedback to update a machine learning model, as described further herein with respect to FIGS. 9 and 10. In some implementations, training module 449 can be implemented as training module 1001 of FIG. 10.

In some implementations, one or more of specialized components 430 may be omitted. For example, it is contemplated that weighted average generator 438 can be omitted from specialized components 430, and that the food intake frequency data generator 440 can use a raw number of hand-to-mouth motions and chewing motions or a standard average without implementing a weighted average. In addition, it is contemplated that object recognition module 442, volume estimation module 444, nutritional data retrieval module 446, and nutritional performance data generator 448 can be omitted from specialized components 430 to perform process 500A of FIG. 5A; and that hand-to-mouth motion classifier 434, chewing motion classifier 436, weighted average generator 438, and food intake frequency data generator 440 can be omitted from specialized components 430 to perform process 500B of FIG. 5B, as described further herein.

Figure 4B:
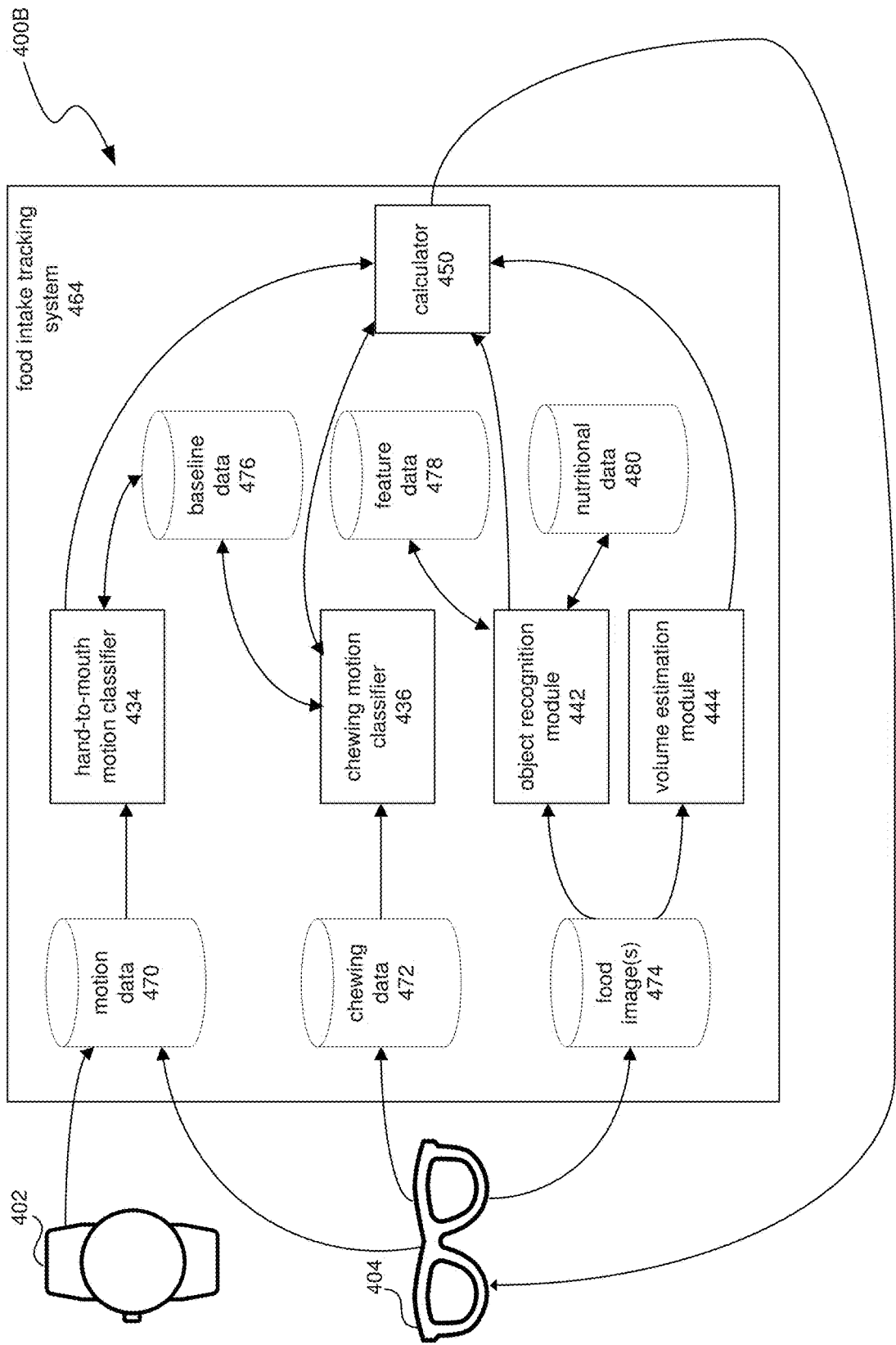
FIG. 4B is a block diagram illustrating the inputs and outputs of the components used in a system employing the disclosed technology.

FIG. 4B is a block diagram illustrating example inputs and outputs of the components used in a system 400B employing the disclosed technology. System 400B can include wearable device 402, smart glasses 404, and food intake tracking system 464. Smart glasses 404 can be an HMD, such as HMD 200 of FIG. 2A or HMD 252 of FIG. 2B. Food intake tracking system 464 can be implemented as food intake tracking system 164 of FIG. 1 in some implementations. Wearable device 402 can be any device also wearable by the user of smart glasses 404 that is configured to detect hand-to-mouth motions, such as a smart watch, bracelet, armband, or ring including one or more sensors associated with an inertial measurement unit (IMU).

Wearable device 402 and/or smart glasses 404 can capture motion data 470 that is fed to hand-to-mouth motion classifier 434, as described further herein with respect to FIG. 4A. For example, one or more sensors of an IMU on wearable device 402 (e.g., accelerometer, gyroscope, compass, etc.) can capture motion data that hand-to-mouth motion classifier 434 can determine is indicative of a hand-to-mouth motion. Alternatively or additionally, an image capture device (e.g., a camera) on smart glasses 404 can capture one or more images as motion data 470 that hand-to-mouth motion classifier 434 can analyze and determine as indicative of a hand-to-mouth motion, i.e., a hand approaching, then retreating, from a user's face. Further details regarding identification of hand-to-mouth motions are described herein with respect to block 504 of FIG. 5A.

Smart glasses 404 can capture chewing data 472 using one or more of a variety of methods. For example, one or more sensors of an IMU on smart glasses 404 can capture movement data indicative of repeated up-and-down movement of the jaw as determined by chewing motion classifier 436. In another example, a microphone on smart glasses 404 can capture an audio signal as chewing data 472 that can be compared to known chewing sounds to identify that chewing motions are occurring by chewing motion classifier 436. Further details regarding identification of chewing motions are described herein with respect to block 506 of FIG. 5A.

Once hand-to-mouth motions and chewing motions have been identified, one or both of hand-to-mouth motion classifier 434 or chewing motion classifier 436 can obtain baseline data 476. Baseline data 476 can be any baseline metric associated with a number of hand-to-mouth motions and/or chewing motions, such as an average cumulative number of hand-to-mouth motions and/or chewing motions for that time of day. The number of hand-to-mouth motions, the number of chewing motions, and baseline data 476 can be provided to calculator 450, which may include weighted average generator 438 and/or food intake frequency data generator 440 of FIG. 4A. Calculator 450 can calculate food intake frequency data that can be displayed on smart glasses 404. Further details regarding generation and display of food intake frequency data are described herein with respect to blocks 508 and 510, respectively, of FIG. 5A.

One or more image capture devices (e.g., one or more cameras) on smart glasses 404 can capture food image(s) 474. Further details regarding capture of food image(s) 474 are described herein with respect to block 512 of FIG. 5B. Food image(s) 474 can be provided to object recognition module 442. Object recognition module 442 can analyze the food image(s) 474 to extract features that are compared to feature data 478 of known food types to identify the type of the food in the food image(s) 474. Once identified, object recognition module 442 can, in conjunction with nutritional data retrieval module 446 of FIG. 4A, obtain nutritional data 480 associated with the food type. Object recognition module 442 can output the food type and associated nutritional data 480 to calculator 450. Further details regarding object recognition are provided herein with respect to block 514 of FIG. 5B.

Food image(s) 474 can also be provided to volume estimation module 444. Volume estimation module 444 can perform volume estimation on the food in food image(s) 474, and provide the estimated volume(s) to calculator 450. Further details regarding volume estimation are provided herein with respect to block 516 of FIG. 5B.

Calculator 450, which can include nutritional performance data generator 448 of FIG. 4A, can adjust nutritional data 480 associated with the food for the volume of food estimated by volume estimation module 444. Calculator 450 can generate nutritional performance data as described herein based on the food type and nutritional data 480, adjusted for the estimated volume. Smart glasses 404 can display the nutritional performance data. Further details regarding generation and display of nutritional performance data are described herein with respect to blocks 520 and 522 of FIG. 5B.

Those skilled in the art will appreciate that the components illustrated in FIGS. 1-4B described above, and in each of the flow diagrams discussed below, may be altered in a variety of ways. For example, the order of the logic may be rearranged, substeps may be performed in parallel, illustrated logic may be omitted, other logic may be included, etc. In some implementations, one or more of the components described above can execute one or more of the processes described below.

Figure 5A:
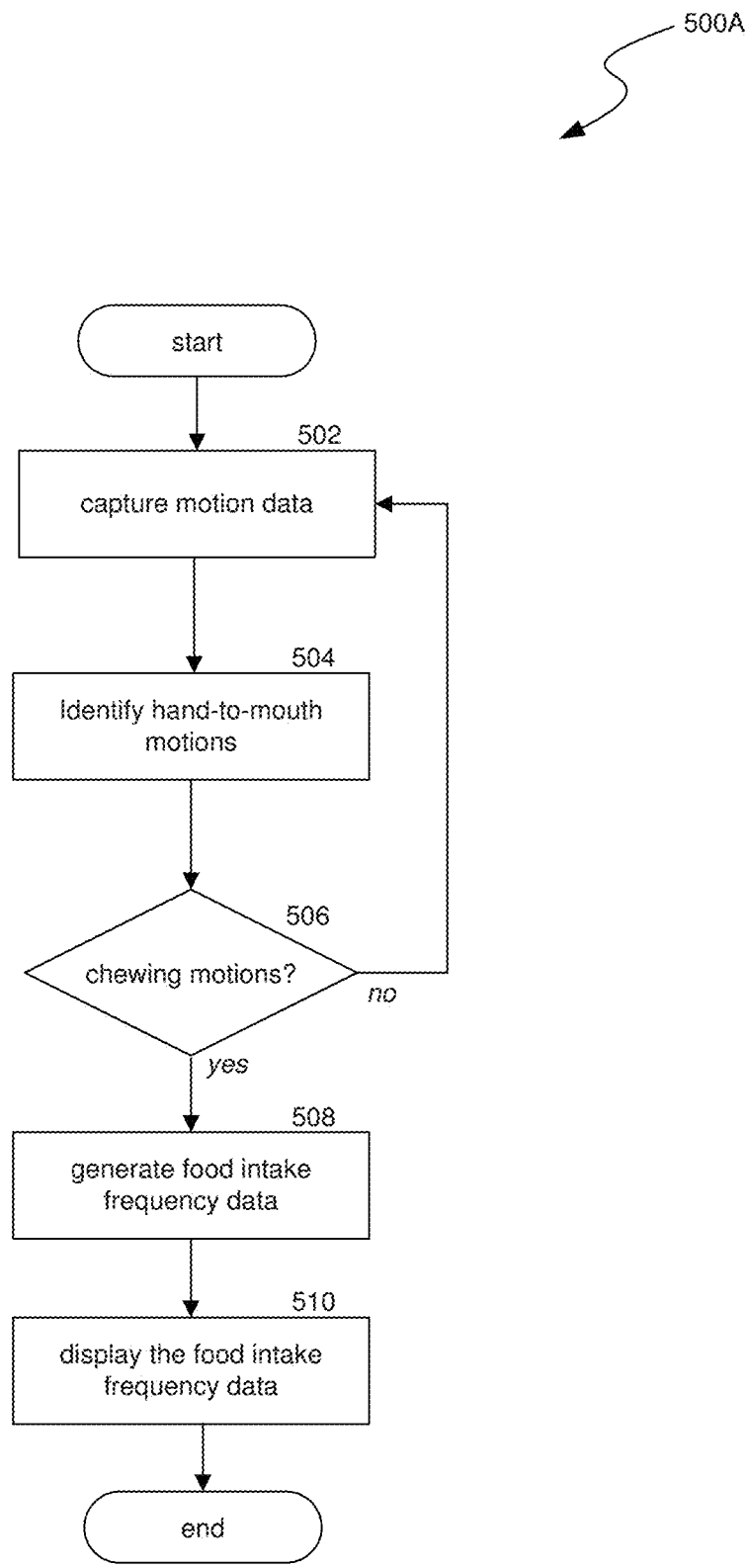
FIG. 5A is a flow diagram illustrating a process used in some implementations of the present technology for quantitative food intake tracking using hand-to-mouth motions and chewing motions.

FIG. 5A is a flow diagram illustrating a process 500A used in some implementations for quantitative food intake tracking using hand-to-mouth motions and chewing. In some implementations, process 500A can be performed as a response to a real-time detection of motion. In some implementations, process 500A can be performed after motion has completed based on saved motion data, e.g., when hand-to-mouth motions or chewing motions have been completed, indicating that the user has finished eating. In some implementations, process 500A can be performed on a schedule or when servers are determined to have available processing capacity. Process 500A can be performed by, for example, food intake tracking system 164 described herein with respect to FIG. 1, or any of the components illustrated and described with respect to FIG. 2A, 2B, or 3.

At block 502, process 500A can capture motion data indicative of motion by the user. Process 500A can capture the motion data using any suitable device internal or external to smart glasses, such as mixed reality HMD 252 described herein with respect to FIG. 2. For example, the motion data can be captured by one or more image capture devices (e.g., one or more cameras) integral with smart glasses. In another example, the motion data can additionally or alternatively be captured by one or more sensors of an inertial measurement unit (IMU) integral with either or both of smart glasses or a wearable device positioned on the wrist or hand, such as a smart watch, wristband, bracelet, or ring. In some implementations, at block 502, process 500A can obtain an audio signal input from a microphone, such as a microphone installed on the smart glasses.

When captured by an IMU, the motion data can be captured by one or more sensors, such as an accelerometer, a gyroscope, a GPS, and/or a magnetometer. The measurements may include the non-gravitational acceleration of the device in the x, y, and z directions; the gravitational acceleration of the device in the x, y, and z directions; the yaw, roll, and pitch of the device; the derivatives of these measurements; the gravity difference angle of the device; and the difference in normed gravitational acceleration of the device. In some implementations, the movements of the device may be measured in intervals, e.g., over a period of 5 seconds.

At block 504, process 500A can analyze the motion data and identify hand-to-mouth motions. For example, when the motion data is captured by an image capture device integral with smart glasses, process 500A can perform object recognition on the captured image(s) to identify a user's hand, and determine that the identified hand is approaching the user's mouth below the smart glasses. In some implementations, process 500A can use a machine learning model to identify hand-to-mouth motions from image(s). For example, process 500A can train a machine learning model with images capturing known hand-to-mouth motions, such as images showing a user's hand near the mouth, approaching the mouth, or holding a utensil, or any combination thereof. Process 500A can identify relevant features in the images, such as edges, curves, and/or colors indicative of fingers, a hand, and/or a utensil. When multiple images are used to capture a single hand-to-mouth motion, process 500A can identify that the relevant features become bigger and/or smaller, representing the hand and/or utensil approaching or retreating from the face. Process 500A can train the machine learning model using these relevant features of known hand-to-mouth motions. Once the model is trained with a sufficient data, process 500A can use the trained model to identify relevant features in newly captured image(s) and compare them to the features of known hand-to-mouth motions. In some implementations, process 500A can use the trained model to assign a match score to the newly captured image(s), e.g., 80%. If the match score is above a threshold, e.g., 70%, process 500A can classify the motion data captured by the image(s) as being indicative of a hand-to-mouth motion. In some implementations, process 500A can further receive feedback from the user regarding whether the identification of the hand-to-mouth motion was correct, and update the trained model accordingly.

In another example, when the motion data is captured by a gyroscope and/or accelerometer in an IMU of a smart watch, process 500A can analyze the motion data to identify features or patterns indicative of a hand-to-mouth motion, as trained by a machine learning model. For example, process 500A can classify the motion data captured by the smart watch as a hand-to-mouth motion based on characteristics of the device movements. Hand-to-mouth motions as used herein refer to movements of the smart watch that are indicative of movement of the user's hand toward his mouth. Exemplary characteristics include changes in angle of the smart watch with respect to gravity. Alternatively or additionally, the device movements may be classified as hand-to-mouth motions based on a comparison of the device movements to stored movements that are known or confirmed to be hand-to-mouth motions. For example, process 500A can train a machine learning model with accelerometer and/or gyroscope data representative of known hand-to-mouth motions. Process 500A can identify relevant features in the data, such as a change in angle of the smart watch within a particular range, separately or in conjunction with movement of the smart watch within a particular range. When new input data is received, i.e., new motion data, process 500A can extract the relevant features from the new accelerometer and/or gyroscope data and compare it to the identified features of the known hand-to-mouth motions of the trained model. In some implementations, process 500A can use the trained model to assign a match score to the new motion data, and classify the new motion data as indicative of a hand-to-mouth motion if the match score is above a threshold, e.g., 75%. Process 500A can further receive feedback from the user regarding whether an identified hand-to-mouth motion is correct to further train the model used to classify motion data as indicative of hand-to-mouth motions.

In some implementations, process 500A can track the gaze of the user wearing the smart glasses when predicting hand-to-mouth motions, e.g., using one or more image capture devices on the smart glasses. If the gaze of the user is away from food being brought to the mouth, process 500A can determine that the hand-to-mouth motions are not indicative of eating and will not use the hand-to-mouth motions to generate food intake frequency data. For example, if the user is scratching his chin, blowing his nose, etc., he will likely not be holding food and/or will not be looking at food coming toward his mouth. However, if the gaze of the user is on food being brought to the mouth (and/or is followed by chewing), process 500A can determine that the hand-to-mouth motions are indicative of eating and use the hand-to-mouth motions to generate food intake frequency data.

At block 506, process 500A determines whether the motions from block 502 and/or the hand-to-mouth motions from block 504 are chewing motions. In some implementations, block 506 can use only one of the outputs from block 502 or 504, in which case the unused block can be skipped above. In other cases, both block can be used.

In some cases, process 500A can also analyze an audio signal, using a machine learning model, to identify sounds consistent with chewing. For example, process 500A can train a machine learning model with audio signal data representative of known chewing sounds. Process 500A can identify relevant features in the data, such as changes in amplitude of the audio signal and/or frequency characteristics indicative of a repeated sound. When new input data is received, i.e., a new audio signal, process 500A can extract the relevant features from the new audio signal and compare it to the identified features of the known chewing sounds of the trained model. In some implementations, process 500A can use the trained model to assign a match score to the new chewing sounds, and classify the new chewing sounds as indicative of chewing if the match score is above a threshold, e.g., 75%. Process 500A can further receive feedback from the user regarding whether an identified chewing sound is correct to further train the model used to classify data as indicative of chewing.

Alternatively or additionally, process 500A can analyze accelerometer data captured by an IMU on the smart glasses to identify subtle repeated motions of a user's head consistent with up and down movement of the jaw. For example, process 500A can classify the motion data captured by the smart glasses as chewing motions based on characteristics of the device movements. Chewing motions as used herein refer to movements of the smart glasses that are indicative of repeated movement of the user's jaw. Exemplary characteristics include changes in angle of the smart glasses with respect to gravity. Alternatively or additionally, the device movements may be classified as chewing motions based on a comparison of the device movements to stored movements that are known or confirmed to be chewing motions. For example, process 500A can train a machine learning model with accelerometer and/or gyroscope data representative of known chewing motions. Process 500A can identify relevant features in the data, such as a change in angle of the smart glasses within a particular range. When new input data is received, i.e., new motion data, process 500A can extract the relevant features from the new accelerometer and/or gyroscope data and compare it to the identified features of the known chewing motions of the trained model. In some implementations, process 500A can use the trained model to assign a match score to the new motion data (e.g., 90%), and classify the new motion data as indicative of a chewing motion if the match score is above a threshold, e.g., 70%. Process 500A can further receive feedback from the user regarding whether an identified chewing motion is correct to further train the model used to classify motion data as indicative of chewing motions.

In some implementations, if process 500A does not identify chewing motions, process 500A can determine that the identified hand-to-mouth motion was not associated with eating, return to block 502, and continue to capture motion data. If process 500A identifies chewing motions at block 506, process 500A can proceed to block 508. At block 508, process 500A can generate food intake frequency data by comparing the hand-to-mouth motions and/or the chewing motions to baseline metrics. For example, process 500A can count the number of hand-to-mouth and/or chewing motions made and compare them to any baseline metric data available, including historical data. For example, the baseline metrics can include at least one of average number of hand-to-mouth motions and/or chewing motions made by the user per meal; average number of hand-to-mouth motions and/or chewing motions made by the user for that particular meal (e.g., breakfast, lunch, dinner, or snack); average number of hand-to-mouth motions and/or chewing motions made by the user by that time of the day; or a maximum or minimum number of hand-to-mouth motions or chewing motions made by the user per meal, for that particular meal, or per day; or any combination thereof. In some implementations, the baseline metric can be any of the above metrics calculated for other users, a plurality of users, or can be based on general nutritional guidelines.

In some implementations, process 500A can calculate a weighted average of the hand-to-mouth motions and the chewing motions. For example, process 500A can weigh the number of hand-to-mouth motions more heavily than the number of chewing motions. Such a weighted average can more accurately reflect the number of bites of food that are eaten, because the number of chewing motions made by a user can be affected by the texture or density of the food being eaten.

At block 510, process 500A can display the food intake frequency data. For example, the food intake frequency data can be displayed textually or graphically on the smart glasses, as described further herein with respect to FIG. 6. In some implementations, process 500A can display the number of hand-to-mouth motions, chewing motions, or the weighted average with respect to the baseline metric such that the user of the smart glasses can easily ascertain his food intake frequency for that meal or that day, and decide whether to continue eating or to stop eating.

Although blocks 502-510 are illustrated as having one iteration in FIG. 5A, it is contemplated that blocks 502-510 can be repeated multiple times, periodically, in response to a trigger, or continuously. For example, blocks 502-510 can be repeated until process 500A detects that the user is done eating (i.e., there are no further hand-to-mouth motions and/or chewing motions), an express indication that the user is done eating (e.g., the user makes an audible announcement, gesture, or selects a button), and/or until the smart glasses are removed or powered off.

Figure 5B:
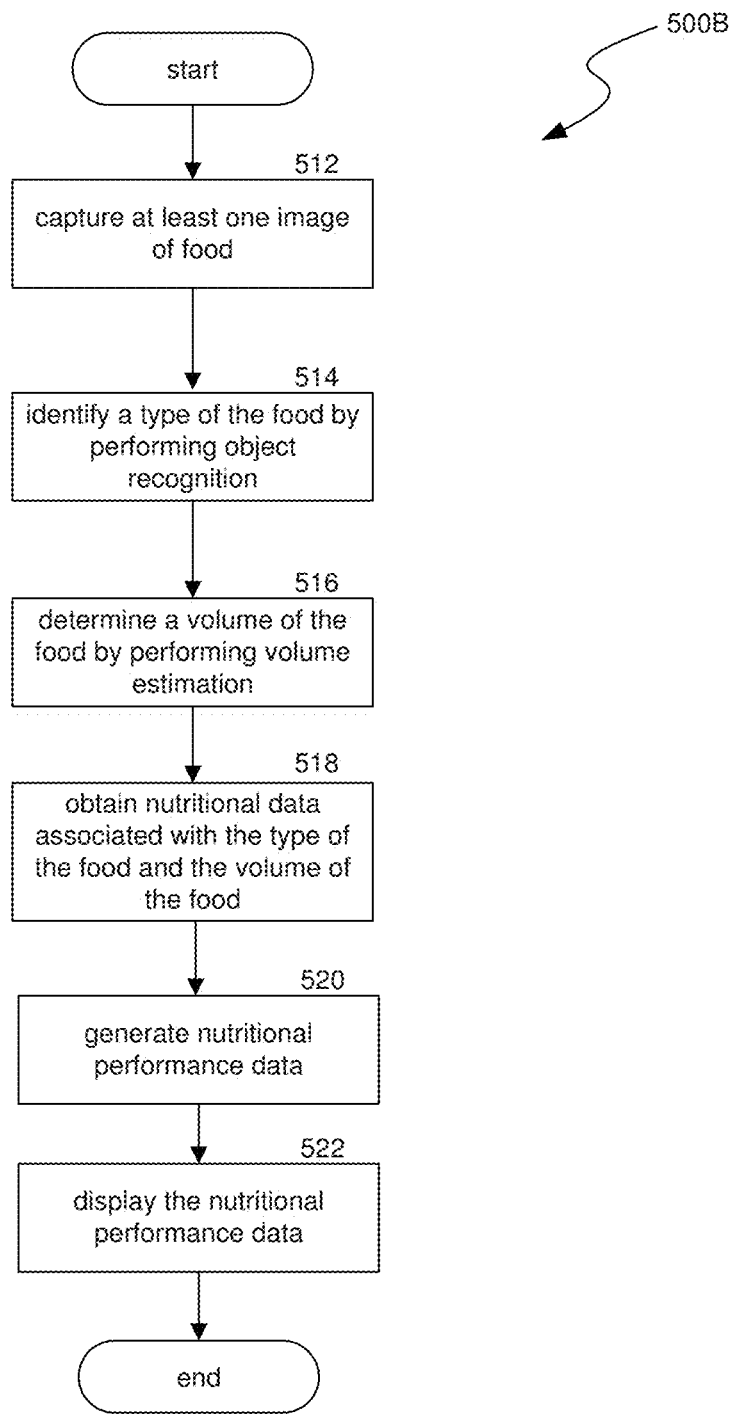
FIG. 5B is a flow diagram illustrating a process used in some implementations of the present technology for quantitative food intake tracking using object recognition and volume estimation from images.

FIG. 5B is a flow diagram illustrating a process 500B used in some implementations of the present technology for quantitative food intake tracking using object recognition and volume estimation from one or more images. In some implementations, process 500B can be performed as a response to a real-time detection of food, as a response to a user indication of food (e.g., an audible alert, a detected gesture, a user selection of a physical or virtual button, etc.), and/or the like. In some implementations, process 500B can be performed after a user has eaten based on one or more saved images of food captured previously. As with process 500A described above with respect to FIG. 5A, process 500B can be performed on a schedule or when servers are determined to have available processing capacity in some implementations. Process 500B can be performed by, for example, food intake tracking system 164 described herein with respect to FIG. 1, or any of the components illustrated and described with respect to FIG. 2A, 2B, or 3.

At block 512, process 500B can capture at least one image of food. For example, one or more image capture devices (e.g., one or more cameras) integral with the smart glasses can capture one or more images of food in the field-of-view of the user. Process 500B can determine that the food within a user's field-of-view is to be consumed by the user based on any number of factors, including at least one of the user's proximity to the food, the user's gaze at the food (e.g., using a camera tracking the eye motion of the user), the user's handling of the food, the user picking up a utensil proximate to the food, or an explicit indication that the user is consuming the food (e.g., audibly, with a gesture, or based on a user's selection of a button), or any combination thereof.

At block 514, process 500B can identify a type of the food by performing object recognition on the at least one image of food. Process 500B can perform object recognition using any suitable technique, such as template matching, color-based matching, active or passive recognition, shape-based recognition, image segmentation and blob analysis, etc., using artificial intelligence techniques. In some implementations, process 500B can apply machine learning algorithms and/or deep learning models in order to learn the features of many different types of food in order to predict and identify food within a particular image. Such features can include, for example, color, texture, edges, corners, shapes, sizes, curves, dimensions, etc. Further details regarding object recognition are described below with respect to FIG. 11.

Figure 9:
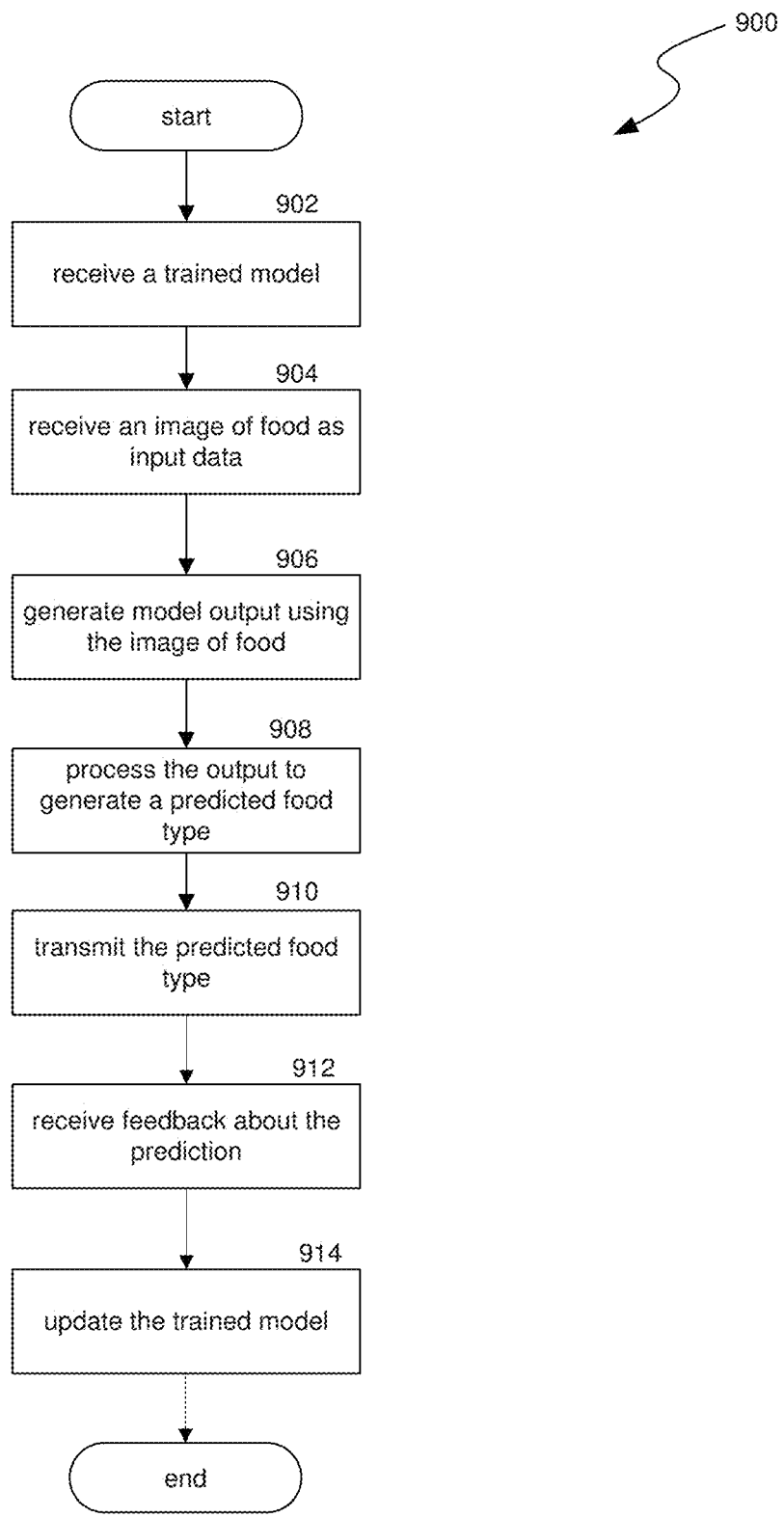
FIG. 9 is a flow diagram illustrating a process used in some implementations for applying and updating a trained model to perform object recognition according to some implementations of the present technology.

In some implementations, process 500B can further predict the type of food using contextual factors, such as the time of day that is the food is being eaten (e.g., morning, noon, night, etc.), where the food is being eaten (e.g., in a dining room, in a restaurant, at a picnic table, etc.), what the user is doing while eating the food (e.g., watching a movie, going for a walk, etc.), how the user is eating the food (e.g., with a knife and fork, with chopsticks, with hands, etc.), and the like, as described further herein with respect to FIG. 9. Exemplary methods of applying machine learning techniques to perform object recognition are described further herein with respect to FIGS. 9-11.

In some implementations, process 500B can further predict the type of food using user metadata associated with that user and/or other users. The user metadata can include any information specific to a user that could be relevant to what type of food she may consume. For example, the user metadata can include a user's height, weight, dietary restrictions, allergies, health concerns, eating goals, exercise habits, gender, nationality, etc. The user metadata can further include information regarding past eating habits of the user, e.g., information regarding food items that the user frequently eats, rarely eats, never eats, etc. In some implementations, process 500B can access user metadata for one or more other users (e.g., similar users as indicated by the metadata) to predict the type of food being eaten by that particular user.

In some implementations, process 500B can display the identified type of the food to the user on the smart glasses. Process 500B can receive explicit or implicit feedback from the user regarding whether the identified type of food is correct. For example, the user can audibly announce or otherwise indicate that the identified type of food is correct or incorrect, and if incorrect, can announce the correct type of food. Process 500B can use this feedback to update a machine learning model, as is described further herein with respect to FIGS. 9-11. In some implementations, process 500B can receive audio input from the user identifying the type of food prior to display of the identified food type, and the identified type of food and images of the food can be used to further train the machine learning model as a known food type having particular features.

At block 516, process 500B can determine a volume of the food by performing volume estimation on the at least one image of food. Process 500B can perform volume estimation by any suitable method. In one example, process 500B can use a depth camera integral with the smart glasses that can evaluate depth and distance of the food in order to predict a volume of the food or process 500B can use a machine learning model trained to estimate depth data and/or volume data from traditional images. For example, a machine learning model can be trained with pairs of images taken from the same position—one taken with a depth camera and one with a traditional camera, where a model can be trained by receiving the traditional image, estimating depth data for each pixel, and then updating model parameters based on a comparison of the predicted pixel depths to those measured in the corresponding depth image. In another example, process 500B can illuminate the food with light (e.g., laser or infrared light) and determine depth and estimate volume e.g., based on deformation of a light pattern or time of flight readings. In some implementations, process 500B can estimate the volume of food by comparing the size of the food in one or more images to an object of known size. For example, process 500B can compare the size of the food in the image(s) to the size of a utensil (e.g., fork, spoon, knife, etc.), plate, napkin, placemat, cup, or other table setting object of relatively standard size.

In some implementations, process 500B can use two cameras to capture the food from different angles. Because the distance between the center of the two camera lenses are known, as well as the distances between the two camera lenses to the food, process 500B can predict the 3D dimensions of the food in order to determine its volume. In some implementations, process 500B can use multiple images of the food captured by one or more cameras (e.g., as a user moves his head around the food or looks at the food from different angles) such that a 3D or volumetric model of the food can be created to estimate volume. However, it is also contemplated that process 500B can apply a machine learning model to a single image of the food in order to predict depth of the food, e.g., by analyzing lighting and color of the food on a pixel-by-pixel basis with respect to the distance of the camera from the food.

In some implementations, process 500B can perform volume estimation integrally with object recognition. For example, process 500B can perform edge detection, image segmentation, and feature extraction to both identify the food type and find its dimensions. In some implementations, process 500B can estimate the dimensions of the food solely from the captured images. Alternatively or additionally, process 500B can estimate the dimensions of the food by comparing the images of the food to stored images of food of the identified food type having known dimensions and/or volumes. Once the dimensions of the food are known, process 500B can generate a 3D representation of the food, and take any number of slices or samples of the 3D representation to estimate the overall volume of the food.

Similar to that described above with respect to the type of food, in some implementations, process 500B can display the predicted volume of food to the user on the smart glasses. Process 500B can receive explicit or implicit feedback from the user regarding whether the predicted volume of food is correct. For example, the user can audibly announce or otherwise indicate that the predicted volume of food is correct or incorrect, and if incorrect, can announce the correct volume of food. Process 500B can use this feedback to update a machine learning model. In some implementations, process 500B can receive audio input from the user identifying the volume of food prior to display of the predicted food volume, and the identified volume of food and images of the food can be used to further train the machine learning model as a known food volume based on a particular image.

At block 518, process 500B can obtain nutritional data associated with the type of food and the volume of the food. The nutritional data can include metrics, for example, such as calories, total fat, saturated fat, sugar, carbohydrates, cholesterol, protein, sodium, vitamins, minerals, etc., adjusted for the identified volume of the food. For example, process 500B can obtain the following nutritional data for 3 ounces of filet mignon: 227 calories, 15 g of total fat, 6 g of saturated fat, 82 mg of cholesterol, 46 mg of sodium, 280 mg of potassium, 0 g of carbohydrates, and 22 g of protein.

At block 520, process 500 can generate nutritional performance data by comparing the nutritional data to a nutritional benchmark for the user. The nutritional benchmark can be based on any desired goal by or for a user (e.g., weight loss, muscle gain, iron intake increase, sugar intake decrease, fat intake decrease, sodium intake decrease, etc.), and can include, for example, a minimum, average, or maximum amount of any particular metric(s) associated with the food for that particular meal, that day, that week, that month, etc. In some implementations, the nutritional benchmark can be based on goals established by or for other users, or can be based on general nutritional guidelines.

At block 522, process 500B can display the nutritional performance data to the user on the smart glasses. For example, process 500B can display the nutritional performance data textually or graphically on the smart glasses, as described further herein with respect to FIG. 7. In some implementations, process 500B can display the nutritional data and/or the nutritional performance data with respect to the nutritional benchmark such that the user of the smart glasses can easily ascertain her food intake for that meal or that day, and decide to continue or modify her eating behavior.

Although blocks 512-522 are illustrated as having one iteration in FIG. 5B, it is contemplated that blocks 512-522 can be repeated multiple times, periodically, in response to a trigger, or continuously. For example, blocks 512-522 can be repeated until process 500B detects that the user is done eating (e.g., food is no longer present in the captured images), an express indication that the user is done eating (e.g., the user makes an audible announcement, gesture, or selects a button), and/or until the smart glasses are removed or powered off. In addition, one or more of blocks 512-522 can be repeated until all of the food items in a captured image are identified.

In some implementations, process 500B can capture at least one additional image of the food after the user is done eating as determined by one or more of the above methods. Process 500B can then perform object recognition and volume estimation on any uneaten food. Process 500B can adjust the nutritional data and/or nutritional performance data to reflect which food and how much food was actually consumed by the user.

Although process 500A of FIG. 5A and process 500B of FIG. 5B are illustrated separately herein, it is contemplated that both process 500A and process 500B can be performed consecutively or concurrently in parallel, and that data gleaned from one process can be used to perform the other. For example, process 500A can determine that the user has finished eating based on the cessation of hand-to-mouth motions and chewing motions. Process 500B can then perform object recognition and volume estimation on the remaining food as described above in order to adjust the nutritional data and/or nutritional performance data to reflect the amount of food actually consumed by the user.

In another example, process 500B of FIG. 5B can perform blocks 512-514 to identify the food on a plate, then capture subsequent images of hand-to-mouth motions identified at block 504 of FIG. 5A to estimate the volume of food actually being consumed. Process 500B can perform blocks 516-522 either continuously in real-time as the food is being consumed, or after a meal has been completed.

Figure 6:
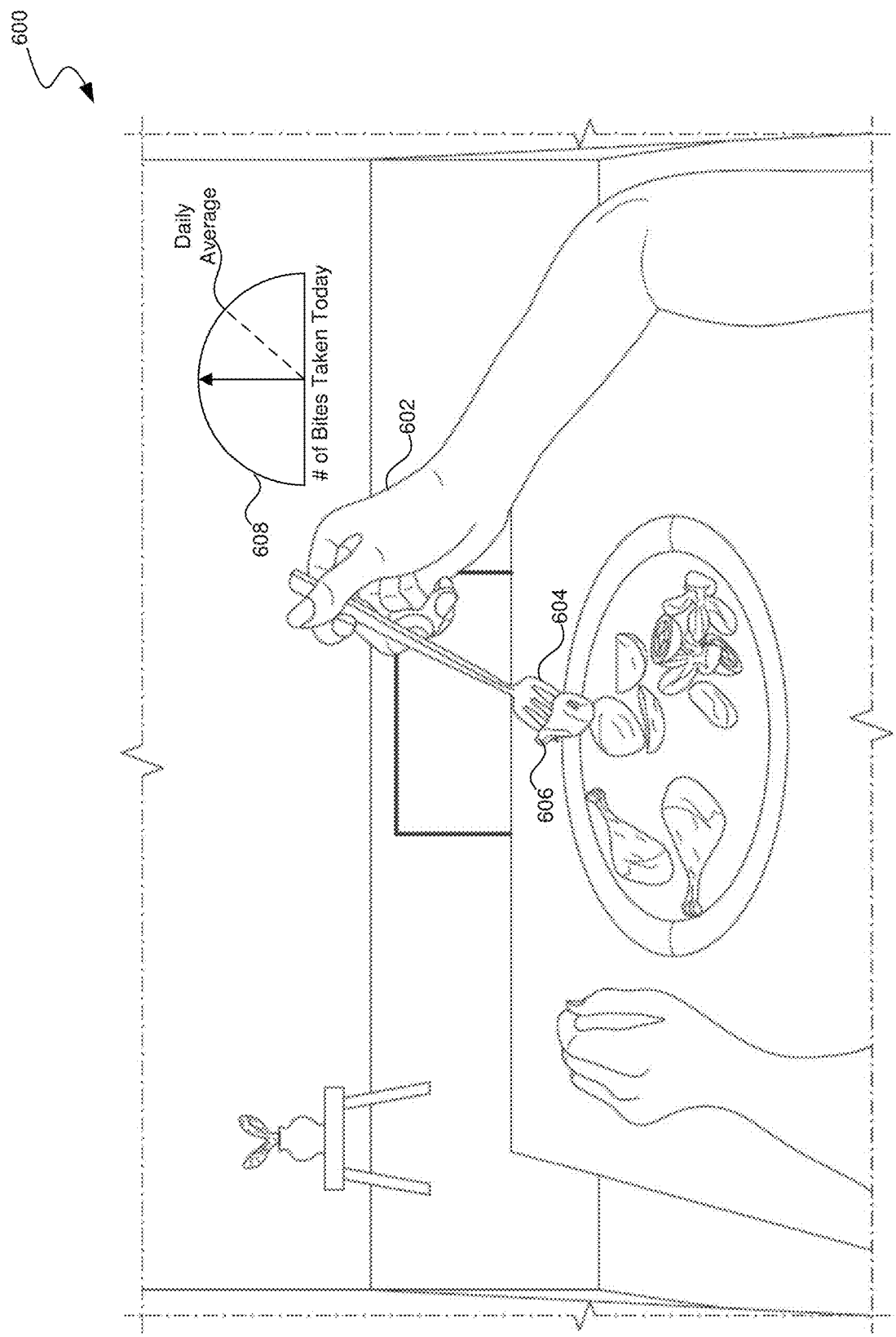
FIG. 6 is a conceptual diagram illustrating an example view through the smart glasses of a user performing a hand-to-mouth motion according to some implementations of the present technology.

FIG. 6 is a conceptual diagram illustrating an example view 600 through the smart glasses of a user performing a hand-to-mouth motion according to some implementations of the present technology. The smart glasses can be any of the HMDs or smart glasses described herein, such as HMD 200 of FIG. 2A, HMD 252 of FIG. 2B, smart glasses 404 of FIG. 4B, etc. View 600 shows a user's hand 602 holding a fork 604 with food 606 on it coming toward the user's face, below the smart glasses.

View 600 can be, for example, captured as an image by an image capture device (e.g., a camera) located on the smart glasses. In some embodiments, the food intake tracking system described herein (e.g., food intake tracking system 164 of FIG. 1 and/or food intake tracking system 464 of FIG. 4B) can perform object recognition on the image (or multiple consecutive images) to identify at least one of the user's hand 602 near the user's mouth, the user's hand 602 coming toward the user's mouth, the user holding the fork 604 in his hand 602, or the user's fork 604 having food 606 on it, or any combination thereof. The food intake tracking system can be trained and perform object recognition for such items in a similar manner as is described herein with respect to identifying food, and is thus not described here in detail. In some implementations, the food intake tracking system can alternatively or additionally identify a hand-to-mouth motion using a wearable device proximate to the user's hand 602 (not shown), as described further herein with respect to block 504 of FIG. 5A.

Once a hand-to-mouth motion is identified, the food intake tracking system can identify any chewing motions, as described further herein with respect to block 506 of FIG. 5A. Throughout the meal, the food intake tracking system can count the number of hand-to-mouth motions and/or chewing motions and generate food intake frequency data 608 that can be overlaid onto view 600, either as the user is eating in real-time, or after the meal is complete. In FIG. 6, food intake frequency data 608 is a number of bites taken in that day as compared to the user's total daily average number of bites for that day.

Figure 7:
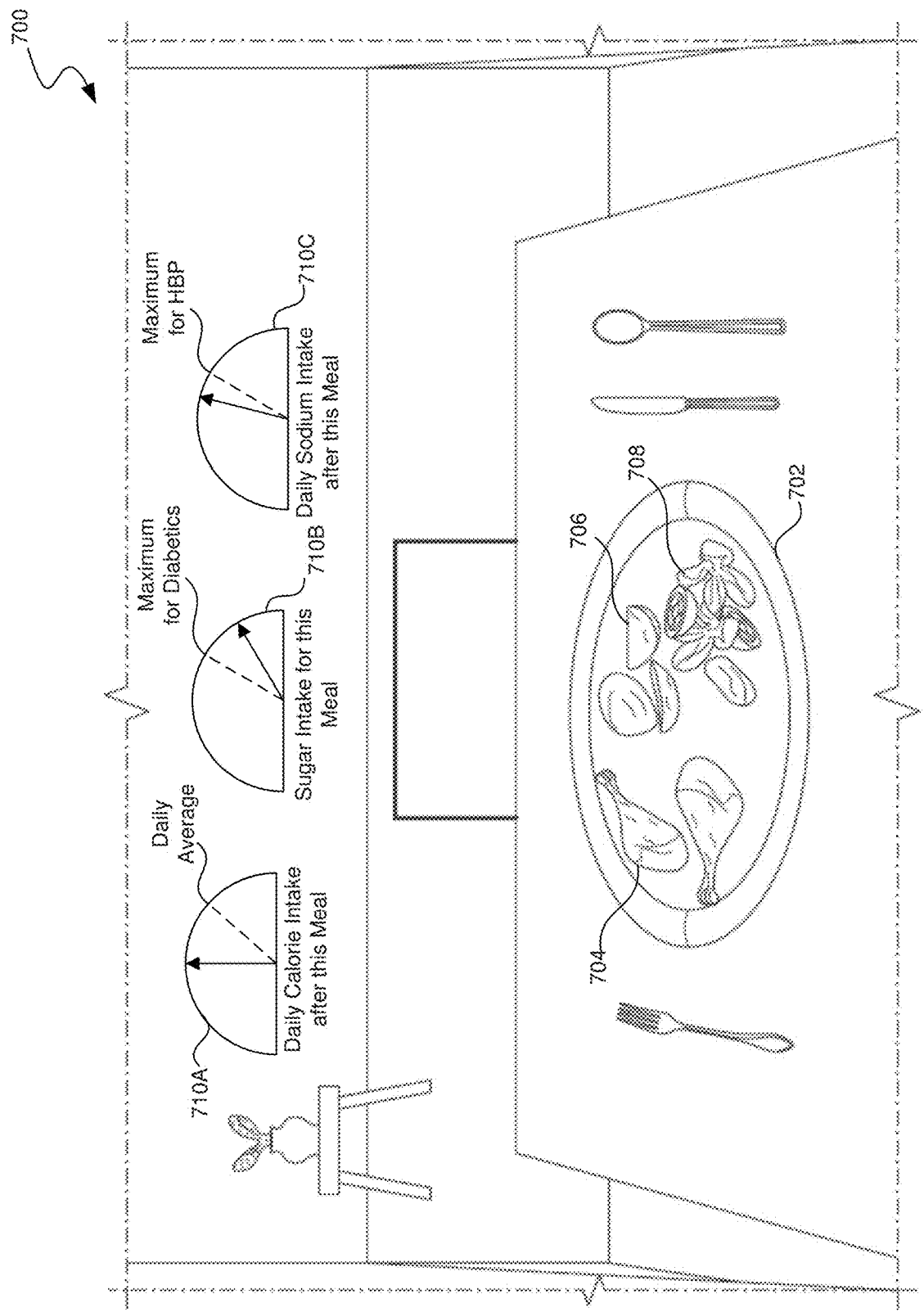
FIG. 7 is a conceptual diagram illustrating an example view through the smart glasses of a plate of food that is about to be eaten according to some implementations of the present technology.

FIG. 7 is a conceptual diagram illustrating an example view 700 through the smart glasses of a plate 702 of food that is about to be eaten by a user according to some implementations of the present technology. The smart glasses can be any of the HMDs or smart glasses described herein, such as HMD 200 of FIG. 2A, HMD 252 of FIG. 2B, smart glasses 404 of FIG. 4B, etc. View 700 shows chicken 704, potatoes 706, and brussels sprouts 708 on plate 702.

View 700 can be, for example, captured as an image by an image capture device (e.g., a camera) located on the smart glasses. In some embodiments, the food intake tracking system described herein (e.g., food intake tracking system 164 of FIG. 1 and/or food intake tracking system 464 of FIG. 4B) can perform object recognition on the image to identify chicken 704, potatoes 706, and brussels sprouts 708, as described further herein with respect to block 514 of FIG. 5B. The food intake tracking system can further perform volume estimation on chicken 704, potatoes 706, and brussels sprouts 708 to determine their respective volumes, as described herein with respect to block 516 of FIG. 5B.

Once the types of food and volumes have been identified, the food intake tracking system can display nutritional performance data 710A-710C overlaid onto view 700. In this example, nutritional performance data 710A includes the user's daily calorie intake after this meal as compared to the user's total daily average caloric intake; nutritional performance data 710B includes the sugar intake for this meal as compared to the maximum sugar intake per meal recommended for diabetics; and nutritional performance data 710C includes the user's total daily sodium intake after this meal as compared to the maximum daily sodium intake recommended for people with high blood pressure. Further examples of nutritional performance data are described herein with respect to block 520 of FIG. 5B.

In some embodiments, the food intake tracking system can further display the identified food types and estimated volumes for each type of food (not shown). The user can provide feedback regarding whether the identified food types and/or estimated volumes for each food type are correct, e.g., audibly as received by a microphone on the smart glasses, or through a gesture detected by the smart glasses. The food intake tracking system can use the feedback to refine either or both of its machine learning models for objection recognition or volume estimation, as described further herein with respect to FIGS. 9 and 10.

Figure 8:
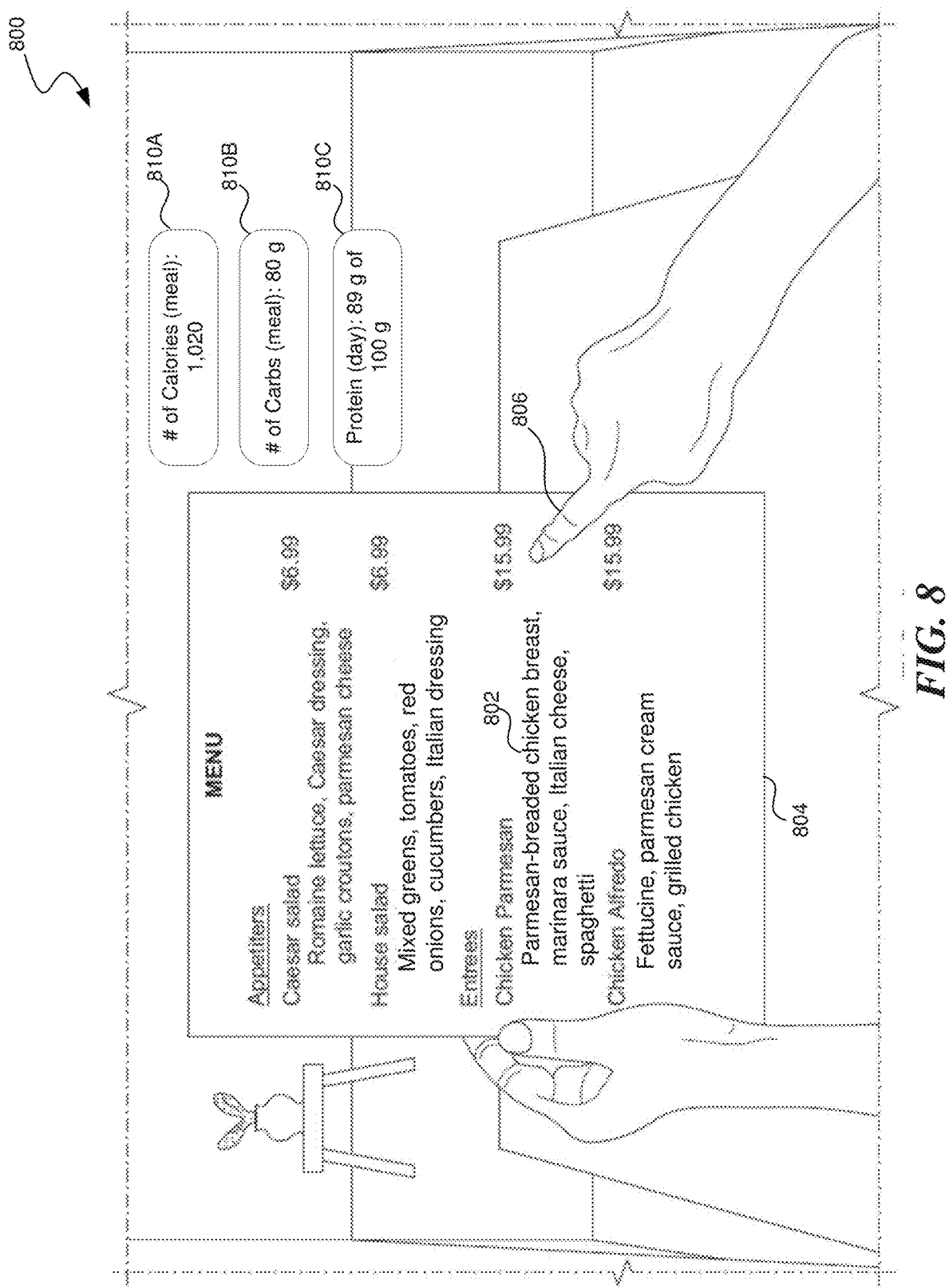
FIG. 8 is a conceptual diagram illustrating an example view through the smart glasses of a user selecting food from a menu according to some implementations of the present technology.

FIG. 8 is a conceptual diagram illustrating an example view 800 through the smart glasses of a user selecting a menu item 802 from a menu 804 according to some implementations of the present technology. The smart glasses can be any of the HMDs or smart glasses described herein, such as HMD 200 of FIG. 2A, HMD 252 of FIG. 2B, smart glasses 404 of FIG. 4B, etc. View 800 shows the user's finger 806 pointing at menu item 802.

View 800 can be, for example, captured as an image by an image capture device (e.g., a camera) located on the smart glasses. In some embodiments, the food intake tracking system (e.g., food intake tracking system 164 of FIG. 1 and/or food intake tracking system 464 of FIG. 4B) described herein can perform object recognition on the image to identify the user's finger 806 pointing at menu item 802. The food intake tracking system can be trained and perform object recognition for the user's finger 806 in a similar manner as is described herein with respect to identifying food, and is thus not described here in detail. Alternatively or additionally, the user can audibly announce the menu item 802 (e.g., when ordering from a waiter), which can be detected by a microphone on or proximate to the smart glasses, and processed using speech recognition techniques.

Once the finger 806 is detected, the food intake tracking system can perform textual analysis on menu item 802 proximate to finger 806 to identify what the user has selected to eat. In some embodiments, after the food arrives, the food intake tracking system can capture one or more images of the food and perform object recognition to further train the machine learning model with a known food item, as described further herein with respect to FIGS. 10 and 11. The food intake tracking system can perform volume estimation on the image(s) to determine the volume of food, as described further herein with respect to block 516 of FIG. 5B.

Once the types of food and volumes have been identified, the food intake tracking system can display nutritional performance data 810A-810C overlaid onto view 800. In this example, nutritional performance data 810A includes the number of calories in this meal; nutritional performance data 810B includes the number of carbohydrates for this meal; and nutritional performance data 810C includes the user's total daily protein intake after this meal as compared to the user's daily target protein intake. Further examples of nutritional performance data are described herein with respect to block 520 of FIG. 5B.

FIG. 9 is a flow diagram illustrating a process 900 used in some implementations for applying and updating a trained model to perform object recognition according to some implementations of the present technology. At block 902, process 900 can receive a trained model configured to perform object recognition. In some implementations, process 900 can train the model using a collection of images having known food items and applying a feature extraction algorithm to manually extract features of the image, such as edge or corner features, that can be used to differentiate between the objects. In some implementations, process 900 can train the model by analyzing a large set of training images with known food items and automatically learning the food items' inherent features. Process 900 can map the features of the training images into a classification space identifying the candidate food item associated with those features.

At block 904, process 900 can receive a new image of food as input data. For example, as described above with respect to block 512 of FIG. 5B, process 900 can capture at least one image of food. For example, one or more image capture devices (e.g., one or more cameras) integral with the smart glasses can capture one or more images of food in the field-of-view of the user.

In some implementations, process 900 can also receive contextual factors surrounding the image of food, such as where the image was captured (e.g., in the living room, at a movie theater, at a restaurant, in an office, etc.), when the image was captured (e.g., morning, noon, night, late night, on a holiday, on a weekend, etc.), audio occurring when the image was captured (e.g., a user discussing or announcing what he is going to eat, conversations, etc.), what the user was doing when the image was captured (e.g., watching a movie, working on a computer, etc.), and/or any other contextual data that may be relevant to what type of food a user might eat, such as environmental factors (e.g., the temperature, the weather, etc.).

In some implementations, process 900 can also receive user metadata, such as identifying information associated with the user (e.g., age, gender, nationality, ethnicity, height, weight, etc.), health concerns associated with the user (e.g., diabetic, high blood pressure, overweight, anemic, etc.), activity level of the user (e.g., very active, sedentary, number of steps per day, etc.), food items previously or often consumed by the user (or similar users), and/or the like.

At block 906, process 900 can generate an output using the image of food, the trained model, any user metadata, and any contextual factors. In some implementations, based on the input data, process 900 can extract relevant features from the image of food and map the features as data points or an output vector in the classification space created using the training data.

At block 908, process 900 can process the output to generate a predicted food type in the image. In some implementations, process 900 can generate a match score between the output (i.e., the mapped features of the food) and the features of candidate food types in the classification space by calculating a distance between the output and the candidate food items. The match score can be any numerical or textual value or indicator, such as a statistic or percentage. Process 900 can identify the predicted food type based on, for example, the candidate food item having the highest match score to the output.

At block 910, process 900 can output the predicted food type. In some implementations, process 900 can output the predicted food type to a display on the smart glasses worn by the user via an interface. In some implementations, process 900 can output the predicted food type to a nutritional data retrieval module, such as nutritional data retrieval module 446 of FIG. 4A.

At block 912, process 900 can receive feedback about the predicted food type. In some implementations, the feedback can be explicit, e.g., the user audibly confirms that the predicted food type is correct, the user audibly announces the predicted food type is incorrect and/or identifies the correct food type, the user selects a virtual button indicating that the predicted food type is correct or incorrect, the smart glasses capture an image with textual identification of the food type, etc. In some implementations, the feedback can be implicit, e.g., the user does not correct the predicted food type. The user can provide feedback by the same or a different interface by which the predicted food type was output.

At block 914, process 900 can update the trained model. For example, process 900 can use the feedback data to identify whether the predicted food type was correct or incorrect (and if incorrect, what the correct food type was, if available), and use that information as a comparison factor to update the model and/or the classification space. In some implementations, process 900 can weigh the current training data more heavily than the initial or past training data, as the later training data can be considered more relevant and/or accurate. Although illustrated as a single process 900 in FIG. 9, it is contemplated that process 900 can be performed multiple times and/or repeatedly, either consecutively or concurrently, as additional images are received.

Some implementations of the food intake tracking system can include a machine learning component, such as a neural network, that is trained using a variety of data, including images of known food items, past food items consumed by the user or similar users, metadata associated with the user, contextual factors, and whether the user identified a predicted food type as correct or incorrect. Some implementations can feed input data including an image of food, user metadata, and contextual factors into the trained machine learning component, and based on the output, can generate a predicted food type. Some implementations provide this predicted food type to a user via a display on smart glasses. Some implementations receive feedback about the predicted food type to further enhance the trained model.

A "machine learning model," as used herein, refers to a construct that is trained using training data to make predictions or provide probabilities for new data items, whether or not the new data items were included in the training data. For example, training data for supervised learning can include items with various parameters and an assigned classification. A new data item can have parameters that a model can use to assign a classification to the new data item. As another example, a model can be a probability distribution resulting from the analysis of training data, such as a likelihood of an n-gram occurring in a given language based on an analysis of a large corpus from that language. Examples of models include: neural networks, support vector machines, decision trees, Parzen windows, Bayes, clustering, reinforcement learning, probability distributions, decision trees, decision tree forests, and others. Models can be configured for various situations, data types, sources, and output formats.

In some implementations, the trained model can be a neural network with multiple input nodes that receive input data including an image of food, any user metadata, and any contextual factors. The input nodes can correspond to functions that receive the input and produce results. These results can be provided to one or more levels of intermediate nodes that each produce further results based on a combination of lower level node results. A weighting factor can be applied to the output of each node before the result is passed to the next layer node. At a final layer, ("the output layer,") one or more nodes can produce a value classifying the input that, once the model is trained, can be used to predict a food type in the image. In some implementations, such neural networks, known as deep neural networks, can have multiple layers of intermediate nodes with different configurations, can be a combination of models that receive different parts of the input and/or input from other parts of the deep neural network, or are convolutions or recurrent—partially using output from previous iterations of applying the model as further input to produce results for the current input.

A machine learning model can be trained with supervised learning, where the training data includes images of known food items, any user metadata, and any contextual factors as input and a desired output, such as a prediction of a food type. A current image of a food item can be provided to the model. Output from the model can be compared to the desired output for that food type, and, based on the comparison, the model can be modified, such as by changing weights between nodes of the neural network or parameters of the functions used at each node in the neural network (e.g., applying a loss function). After applying each of the factors in the training data and modifying the model in this manner, the model can be trained to evaluate new input data.

Some implementations of the food intake tracking system can include a deep learning component. A "deep learning model," as used herein with respect to object recognition, refers to a construct trained to learn by example to perform classification directly from images. The deep learning model is trained by using a large set of labeled data and applying a neural network as described above that includes many layers. With respect to object recognition from images, the deep learning model in some implementations can be a convolutional neural network (CNN) that is used to automatically learn an object's inherent features to identify the object. For example, the deep learning model can be an R-CNN, Fast R-CNN, or Faster-RCNN. In some implementations, object recognition can be performed using other object recognition approaches, such as template matching, image segmentation and blob analysis, edge matching, divide-and-conquer search, greyscale matching, gradient matching, pose clustering, geometric hashing, scale-invariant feature transform (SIFT), histogram of oriented gradients (HOG), region-based fully convolutional network (R-FCN), single shot detector (SSD), spatial pyramid pooling (SPP-net), etc.

Figure 10:
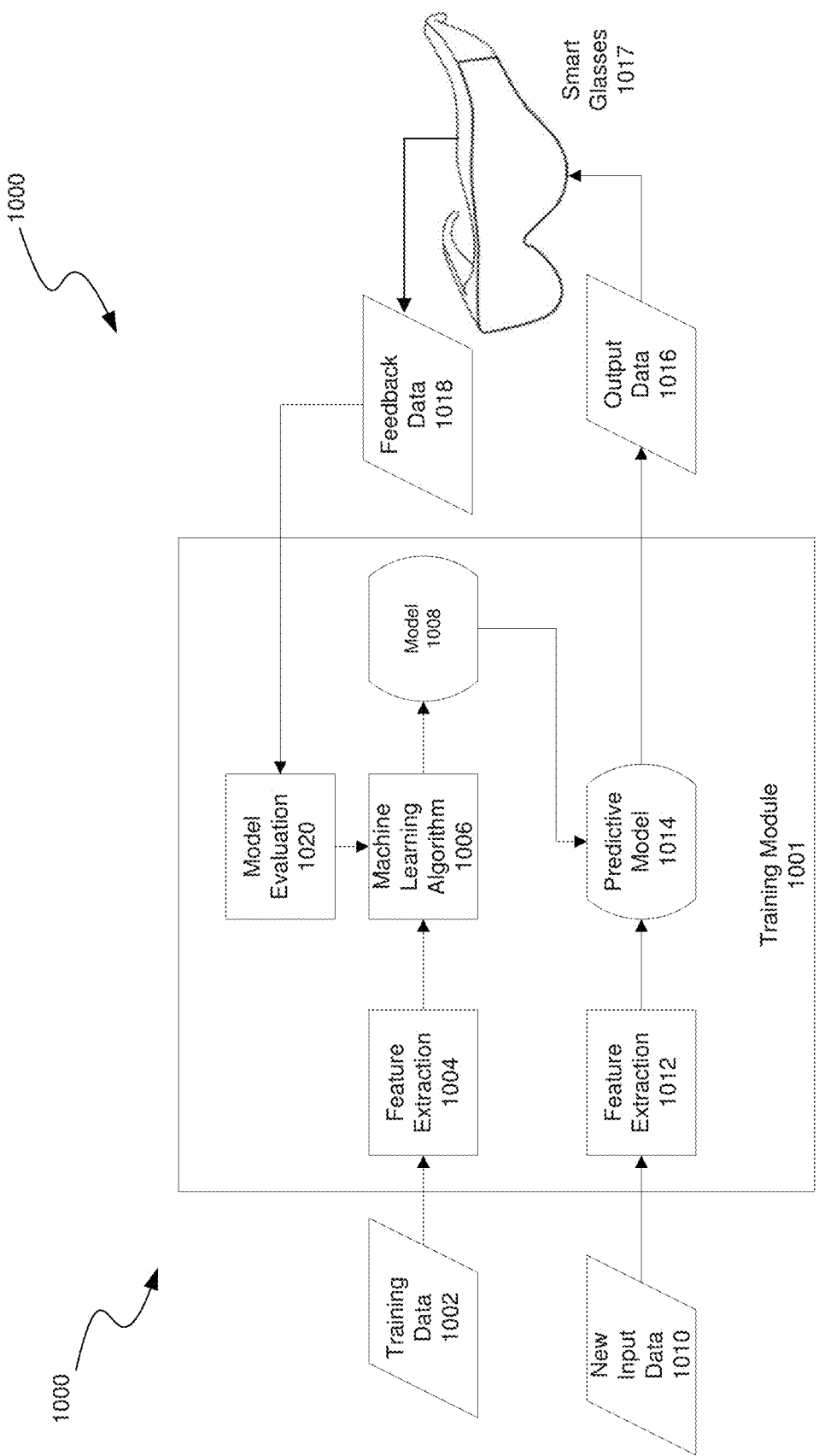
FIG. 10 is a block diagram illustrating an overview of a machine learning system that can be applied to perform object recognition according to some implementations of the present technology.

FIG. 10 is a block diagram illustrating an overview of a machine learning system 1000 that can be applied to perform object recognition according to some implementations of the present technology. In a training phase, system 1000 can feed raw training data 1002 (e.g., images of labeled food items, user metadata, contextual factors, etc.) into feature extraction 1004 of training module 1001 to select useful features (e.g., corners, edges, colors, textures, shapes, sizes, etc.) from all available features. As described further herein with respect to FIG. 9, the contextual factors can include where an image of food is taken, when an image of food is taken, what the user was doing when the image was captured, environmental factors (e.g., temperature, weather, etc.), etc., and can be obtained using any suitable method.

System 1000 can feed the extracted features to machine learning algorithm 1006. Machine learning algorithm 1006 can identify a model 1008 that maps the image of food and any available user metadata and contextual factors to predicted food types, and uses past feedback to identify whether the predictions were correct. In some implementations, model 1008 can be a neural network. System 1000 can repeat the training phase until a suitable accuracy level is reached, e.g., as identified by applying a loss function, such as when a sufficient amount of training data 1002 has been processed and predictions made by model 1008 do not deviate too far from actual results. As appreciated by one skilled in the art, if model 1008 is a deep learning model, a large amount of training data may be needed to make accurate predictions.

In a predicting phase, system 1000 can feed new input data 1010 into feature extraction 1012 of training module 1001 to select useful features. System 1000 can apply a predictive model 1014 to the extracted features based on the trained model 1008 to generate output data 1016 (e.g., a predicted food type). System 1000 provides output data 1016 to user device 1017, such as the smart glasses. The user of the user device 1017 can provide feedback data 1018 to training module 1001 via user device 1017, such as explicit feedback regarding whether the predicted food type was correct or incorrect, or implicit feedback if a user does not correct the predicted food type.

System 1000 can input the feedback data 1018 into model evaluation 1020 to restart the training phase. Model evaluation 1020 can evaluate predictive model 1014 with metrics, for example. The metrics can include accuracy, precision, F1 score, Mean Squared Error, etc. System 1000 can feed these metrics back into machine learning algorithm 1006 to refine and update model 1008, if necessary, and the predicting phase can be repeated.

Figure 11:
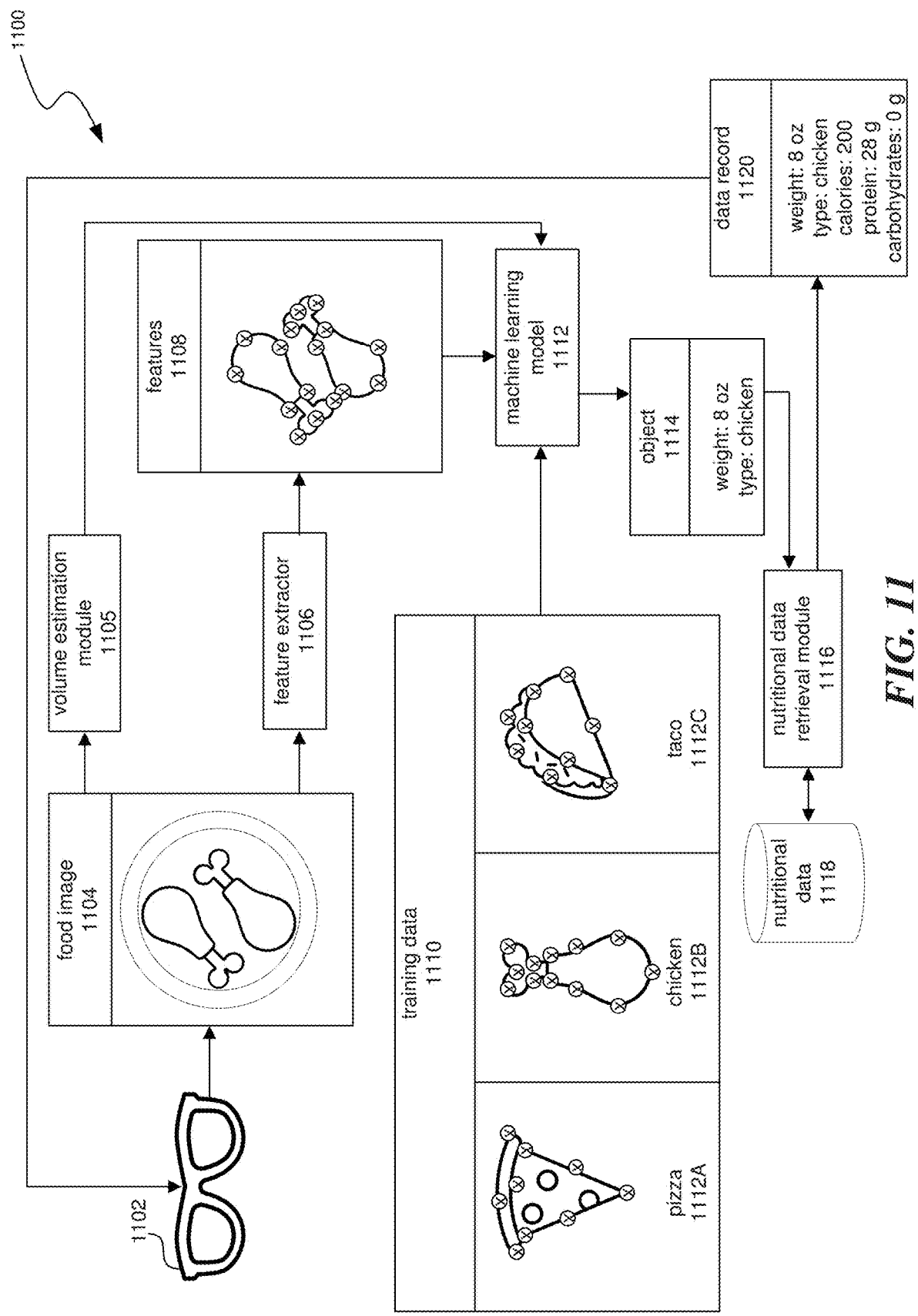
FIG. 11 is a conceptual diagram illustrating an exemplary flow for object recognition and volume estimation according to some implementations of the present technology.

FIG. 11 is a conceptual diagram illustrating an exemplary flow 1100 for object recognition and volume estimation according to some implementations of the present technology. Smart glasses 1102 can capture food image 1104; in this case, a plate of chicken. Smart glasses 1102 can be an HMD, such as any one of HMD 200 of FIG. 2A, HMD 252 of FIG. 2B, smart glasses 404 of FIG. 4B, etc. Food image 1104 can be fed into volume estimation module 1105. Volume estimation module 1105 can analyze food image 1104 to estimate a volume of chicken on the plate, and feed the estimated volume into machine learning model 1112. Further details regarding volume estimation module 1105 are described herein with respect to volume estimation module 444 of FIGS. 4A and 4B.

Food image 1104 can also be fed into a feature extractor 1106 that identifies relevant features 1108 in food image 1104. The relevant features can correspond to, for example, edges, corners, shapes, curvatures, colors, or textures, or any combination thereof. Features 1108 can be fed into machine learning model 1112. Further details regarding feature extraction are described herein with respect to feature extraction 1004 and feature extraction 1012 of FIG. 10.

Machine learning model 1112 can obtain training data 1110 including labeled food items with identified features; for example, pizza 1112A, chicken 1112B, and taco 1112C. Machine learning model 1112 can compare features 1108 to training data 1110 to determine a match score between features 1108 and training data 1110. In this case, machine learning model 1112 can determine that the type of food in food image 1104 is most similar to chicken 1112B. In some implementations, machine learning model 1112 can determine that features 1108 have the highest match score with chicken 1112B. Further details regarding training and applying machine learning model 1112 are described herein with respect to FIG. 10.

Machine learning model 1112 can output data indicating that object 1114 is 8 ounces of chicken, which can be fed into a nutritional data retrieval module 1116. Nutritional data retrieval module 1116 can obtain nutritional data 1118 associated with a particular serving size of chicken and adjust it for the estimated volume of 8 ounces. Nutritional data retrieval module 1116 can output data record 1120 identifying the volume of food, food type, and nutritional data associated with 8 ounces of chicken, e.g., 200 calories, 28 g of protein, and 0 g of carbohydrates. Further details regarding nutritional data retrieval module 1116 are described herein with respect to nutritional data retrieval module 446 of FIG. 4A.

Data record 1120, or any derivative thereof, can be displayed in any suitable means on smart glasses 1102, such as textually or graphically, alongside statistics and goals for that meal or cumulatively that day. Further details regarding display of data record 1120 are described herein with respect to block 510 of FIG. 5A and block 522 of FIG. 5B.

Although described herein with respect to food, it is contemplated that the systems and methods described herein can be used to track consumption of other edible items as well. For example, some implementations can use smart glasses to identify a pill in a user's hand using object recognition, and identify a hand-to-mouth motion with the pill as described further herein. Some implementations can use such information to track whether and when a user has taken their daily medications, vitamins, supplements, etc., and display relevant data to the user regarding the pill on the smart glasses.

For example, with respect to medication, some implementations can identify the type and dosage of the medication being taken, how frequently and when the medication should be taken, how the medication should be taken (e.g., with or without food, with a full glass of water, etc.), warnings and interactions for the medication, etc. Such information can be automatically identified by performing textual analysis on a pill bottle and/or accessing a database of information regarding medications. Additionally or alternatively, some implementations can detect the size, shape, color, dimensions, type (e.g., capsule, tablet, chewable, etc.), and/or any other identifying marks on the pill and search a database of pills having known visual characteristics to identify the type and dosage of the medication. In some implementations, a user of the smart glasses can audibly identify the type and dosage of the medication, as well as any particular instructions with respect to the medication. Further, it is contemplated that the systems and methods described herein can generate reminders and/or alerts to the user of the smart glasses with respect to the medication.

Reference in this specification to "implementations" (e.g., "some implementations," "various implementations," "one implementation," "an implementation," etc.) means that a particular feature, structure, or characteristic described in connection with the implementation is included in at least one implementation of the disclosure. The appearances of these phrases in various places in the specification are not necessarily all referring to the same implementation, nor are separate or alternative implementations mutually exclusive of other implementations. Moreover, various features are described which may be exhibited by some implementations and not by others. Similarly, various requirements are described which may be requirements for some implementations but not for other implementations.

As used herein, being above a threshold means that a value for an item under comparison is above a specified other value, that an item under comparison is among a certain specified number of items with the largest value, or that an item under comparison has a value within a specified top percentage value. As used herein, being below a threshold means that a value for an item under comparison is below a specified other value, that an item under comparison is among a certain specified number of items with the smallest value, or that an item under comparison has a value within a specified bottom percentage value. As used herein, being within a threshold means that a value for an item under comparison is between two specified other values, that an item under comparison is among a middle-specified number of items, or that an item under comparison has a value within a middle-specified percentage range. Relative terms, such as high or unimportant, when not otherwise defined, can be understood as assigning a value and determining how that value compares to an established threshold. For example, the phrase "selecting a fast connection" can be understood to mean selecting a connection that has a value assigned corresponding to its connection speed that is above a threshold.

As used herein, the word "or" refers to any possible permutation of a set of items. For example, the phrase "A, B, or C" refers to at least one of A, B, C, or any combination thereof, such as any of: A; B; C; A and B; A and C; B and C; A, B, and C; or multiple of any item such as A and A; B, B, and C; A, A, B, C, and C; etc.

Although the subject matter has been described in language specific to structural features and/or methodological acts, it is to be understood that the subject matter defined in the appended claims is not necessarily limited to the specific features or acts described above. Specific embodiments and implementations have been described herein for purposes of illustration, but various modifications can be made without deviating from the scope of the embodiments and implementations. The specific features and acts described above are disclosed as example forms of implementing the claims that follow. Accordingly, the embodiments and implementations are not limited except as by the appended claims.

Any patents, patent applications, and other references noted above are incorporated herein by reference. Aspects can be modified, if necessary, to employ the systems, functions, and concepts of the various references described above to provide yet further implementations. If statements or subject matter in a document incorporated by reference conflicts with statements or subject matter of this application, then this application shall control.

We claim:

1. A method for quantitatively tracking food intake using smart glasses, the method comprising:
capturing at least one image of food, and motion data indicative of motion by a user of the smart glasses;
identifying a type of the food by performing object recognition on the at least one image of food;
determining a volume of the food by performing volume estimation on the at least one image of food;
obtaining nutritional data associated with the type of the food and the volume of the food;
generating nutritional performance data by comparing the nutritional data to a nutritional benchmark for the user;
identifying a plurality of hand-to-mouth motions by the user by analyzing the motion data;
identifying a plurality of chewing motions by the user using the smart glasses;
calculating a weighted average of a number of the plurality of hand-to-mouth motions and a number of the plurality of chewing motions, wherein calculating the weighted average includes weighing the number of the plurality of hand-to-mouth motions more heavily than the number of the plurality of chewing motions;
generating food intake frequency data by comparing the weighted average of the number of the plurality of hand-to-mouth motions and the number of the plurality of chewing motions to baseline metrics; and
displaying the nutritional performance data and the food intake frequency data to the user on the smart glasses.

2. The method of claim 1, wherein identifying the plurality of hand-to-mouth motions includes determining that a gaze of the user is focused on food being brought to a mouth of the user.

3. The method of claim 1, wherein the plurality of chewing motions are identified, at least in part, using an audio signal captured by a microphone on the smart glasses.

4. The method of claim 1, further comprising:
receiving feedback from the user explicitly identifying the type of the food; and
updating, based on the feedback, a machine learning model trained to perform the object recognition for the type of the food.

5. The method of claim 1, wherein the volume estimation is performed by analyzing a plurality of images of the food captured at different angles.

6. The method of claim 1, wherein the volume estimation is performed by applying a machine learning model trained to predict depth of the food from one image of the food.

7. The method of claim 1, wherein identifying the plurality of hand-to-mouth motions includes:
applying a machine learning model trained to receive the motion data and categorize the motion data as being or not being indicative of a hand-to-mouth motion.

8. The method of claim 1, wherein the motion data is received from at least one of an inertial measurement unit (IMU) or an image capture device, or a combination thereof.

9. A computer-readable storage medium storing instructions that, when executed by a computing system, cause the computing system to perform a process for quantitatively tracking food intake using smart glasses, the process comprising:
capturing motion data indicative of motion by a user of the smart glasses;
identifying a plurality of hand-to-mouth motions by the user by analyzing the motion data;
identifying a plurality of chewing motions by the user using the smart glasses;
calculating a weighted average of a number of the plurality of hand-to-mouth motions and a number of the plurality of chewing motions, wherein calculating the weighted average includes weighing the number of the plurality of hand-to-mouth motions more heavily than the number of the plurality of chewing motions;
generating food intake frequency data by comparing the weighted average of the number of the plurality of hand-to-mouth motions and the number of the plurality of chewing motions to baseline metrics; and
displaying the food intake frequency data to the user on the smart glasses.

10. The computer-readable storage medium of claim 9, wherein the process further comprises:
capturing at least one image of food;
identifying a type of the food by performing object recognition on the at least one image of food;
determining a volume of the food by performing volume estimation on the at least one image of food;
obtaining nutritional data associated with the type of the food and the volume of the food;
generating nutritional performance data by comparing the nutritional data to a nutritional benchmark for the user; and
displaying the nutritional performance data to the user on the smart glasses.

11. The computer-readable storage medium of claim 9, wherein identifying the plurality of hand-to-mouth motions includes determining that a gaze of the user is focused on food being brought to a mouth of the user.

12. The computer-readable storage medium of claim 9, wherein the plurality of chewing motions are identified, at least in part, using an audio signal captured by a microphone on the smart glasses.

13. The computer-readable storage medium of claim 9, wherein identifying the plurality of hand-to-mouth motions includes:
  applying a machine learning model trained to receive the motion data and categorize the motion data as being or not being indicative of a hand-to-mouth motion.

14. The computer-readable storage medium of claim 9, wherein the motion data is received from at least one of an inertial measurement unit (IMU) or an image capture device, or a combination thereof.

15. A computing system for quantitatively tracking food intake using smart glasses, the computing system comprising:
  one or more processors; and
  one or more memories storing instructions that, when executed by the one or more processors, cause the computing system to perform a process comprising:
    capturing at least one image of food;
    identifying a type of the food by performing object recognition on the at least one image of food;
    determining a volume of the food by performing volume estimation on the at least one image of food;
    obtaining nutritional data associated with the type of the food and the volume of the food;
    generating nutritional performance data by comparing the nutritional data to a nutritional benchmark for a user of the smart glasses;
    identifying a plurality of hand-to-mouth motions by the user by analyzing the motion data;
    identifying a plurality of chewing motions by the user using the smart glasses;
    calculating a weighted average of a number of the plurality of hand-to-mouth motions and a number of the plurality of chewing motions, wherein calculating the weighted average includes weighing the number of the plurality of hand-to-mouth motions more heavily than the number of the plurality of chewing motions;
    generating food intake frequency data by comparing the weighted average of the number of the plurality of hand-to-mouth motions and the number of the plurality of chewing motions to baseline metrics; and
    displaying the nutritional performance data and the food intake frequency data to the user on the smart glasses.

16. The computing system of claim 15, wherein the volume estimation is performed by analyzing a plurality of images of the food captured at different angles.

17. The computing system of claim 15, wherein the volume estimation is performed by applying a machine learning model trained to predict depth of the food from one image of the food.

* * * * *